(12) United States Patent
Diolaiti

(10) Patent No.: US 11,672,616 B2
(45) Date of Patent: Jun. 13, 2023

(54) SECONDARY INSTRUMENT CONTROL IN A COMPUTER-ASSISTED TELEOPERATED SYSTEM

(71) Applicant: INTUITIVE SURGICAL OPERATIONS, INC., Sunnyvale, CA (US)

(72) Inventor: Nicola Diolaiti, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1065 days.

(21) Appl. No.: 16/316,859

(22) PCT Filed: Jul. 14, 2017

(86) PCT No.: PCT/US2017/042228
§ 371 (c)(1),
(2) Date: Jan. 10, 2019

(87) PCT Pub. No.: WO2018/013979
PCT Pub. Date: Jan. 18, 2018

(65) Prior Publication Data
US 2019/0314097 A1    Oct. 17, 2019

Related U.S. Application Data

(60) Provisional application No. 62/362,355, filed on Jul. 14, 2016.

(51) Int. Cl.
*A61B 34/00* (2016.01)
*A61B 34/35* (2016.01)
(Continued)

(52) U.S. Cl.
CPC ............... *A61B 34/25* (2016.02); *A61B 1/04* (2013.01); *A61B 17/00* (2013.01); *A61B 34/35* (2016.02);
(Continued)

(58) Field of Classification Search
CPC ......... A61B 34/00–34/77; A61B 34/35; A61B 2034/2055
See application file for complete search history.

(56) References Cited

U.S. PATENT DOCUMENTS 5,279,309 A * 1/1994 Taylor .................... A61B 34/76
600/595
5,417,210 A * 5/1995 Funda ......................... B25J 9/04
600/109

(Continued)

FOREIGN PATENT DOCUMENTS

CN   102438795 A   5/2012
CN   102869310 A   1/2013
(Continued)

OTHER PUBLICATIONS

Extended European Search Report for Application No. EP17828568.0 dated Feb. 20, 2020, 8 pages.
(Continued)

*Primary Examiner* — Zade Coley
(74) *Attorney, Agent, or Firm* — Artegis Law Group, LLP

(57) ABSTRACT

Systems and methods for a teleoperational system and control thereof are provided. An exemplary system includes a first manipulator configured to support an instrument moveable within an instrument workspace, the instrument having an instrument frame of reference, and includes an operator input device configured to receive movement commands from an operator. The system further includes a control system to implement the movement commands by (Continued)

comparing an orientation of the instrument with an orientation of a field of view of the instrument workspace to produce an orientation comparison. When the comparison does not meet certain criteria, the control system causes instrument motion in a first direction relative to the instrument frame in response to a movement command. When the comparison meets the criteria, the control system causes instrument in a second direction relative to the instrument frame in response to the movement command. The second direction differs from the first direction.

15 Claims, 21 Drawing Sheets

(51) Int. Cl.
 *A61B 90/00* (2016.01)
 *A61B 17/00* (2006.01)
 *A61B 1/04* (2006.01)
 *A61B 90/57* (2016.01)
 *A61B 1/00* (2006.01)
 *A61B 8/12* (2006.01)

(52) U.S. Cl.
 CPC ......... *A61B 90/37* (2016.02); *A61B 1/00193* (2013.01); *A61B 8/12* (2013.01); *A61B 2017/00424* (2013.01); *A61B 2017/00738* (2013.01); *A61B 2090/368* (2016.02); *A61B 2090/571* (2016.02)

(56) References Cited

U.S. PATENT DOCUMENTS

| | | | |
|---|---|---|---|
| 5,572,999 A * | 11/1996 | Funda | A61B 90/11 600/459 |
| 5,792,135 A | 8/1998 | Madhani et al. | |
| 5,876,325 A | 3/1999 | Mizuno et al. | |
| 6,424,885 B1 | 7/2002 | Niemeyer et al. | |
| 6,671,581 B2 | 12/2003 | Niemeyer et al. | |
| 6,788,018 B1 | 9/2004 | Blumenkranz et al. | |
| 6,817,974 B2 | 11/2004 | Cooper et al. | |
| 6,837,883 B2 | 1/2005 | Moll et al. | |
| D536,446 S | 2/2007 | Doll et al. | |
| 7,594,912 B2 | 9/2009 | Cooper et al. | |
| 7,835,823 B2 | 11/2010 | Sillman et al. | |
| 7,955,322 B2 | 6/2011 | Devengenzo et al. | |
| 8,004,229 B2 | 8/2011 | Nowlin et al. | |
| 8,073,528 B2 | 12/2011 | Zhao et al. | |
| D653,338 S | 1/2012 | Mangeshikar et al. | |
| 8,147,503 B2 | 4/2012 | Zhao et al. | |
| 8,271,130 B2 | 9/2012 | Hourtash et al. | |
| 9,089,256 B2 * | 7/2015 | Tognaccini | A61B 1/018 |
| 10,022,195 B2 | 7/2018 | Scholan et al. | |
| 2002/0163499 A1* | 11/2002 | Sauer | H04N 13/344 348/E13.041 |
| 2004/0024311 A1* | 2/2004 | Quaid, III | A61B 90/36 600/428 |
| 2006/0241414 A1 | 10/2006 | Nowlin et al. | |
| 2007/0287992 A1 | 12/2007 | Diolaiti et al. | |
| 2008/0065105 A1 | 3/2008 | Larkin et al. | |
| 2009/0192524 A1 | 7/2009 | Itkowitz et al. | |
| 2009/0326318 A1* | 12/2009 | Tognaccini | A61B 1/04 600/109 |
| 2009/0326553 A1 | 12/2009 | Mustufa et al. | |
| 2009/0326556 A1 | 12/2009 | Diolaiti et al. | |
| 2010/0274087 A1 | 10/2010 | Diolaiti et al. | |
| 2011/0118748 A1* | 5/2011 | Itkowitz | A61B 34/30 606/130 |
| 2011/0276058 A1 | 11/2011 | Choi et al. | |
| 2011/0276059 A1 | 11/2011 | Nowlin et al. | |
| 2011/0282357 A1 | 11/2011 | Rogers et al. | |
| 2011/0282358 A1 | 11/2011 | Gomez et al. | |
| 2012/0059391 A1 | 3/2012 | Diolaiti et al. | |
| 2012/0185098 A1 | 7/2012 | Bosscher et al. | |
| 2013/0096576 A1 | 4/2013 | Cooper et al. | |
| 2013/0211421 A1* | 8/2013 | Abovitz | A61B 90/37 606/130 |
| 2014/0142593 A1 | 5/2014 | Fielding et al. | |
| 2014/0309659 A1 | 10/2014 | Roh et al. | |
| 2014/0378763 A1* | 12/2014 | Atarot | A61B 1/00039 600/109 |
| 2015/0018622 A1* | 1/2015 | Tesar | A61B 17/0218 600/202 |
| 2015/0366625 A1* | 12/2015 | Tognaccini | A61B 1/00183 600/106 |
| 2017/0086931 A1 | 3/2017 | Auld et al. | |
| 2017/0086932 A1 | 3/2017 | Auld et al. | |

FOREIGN PATENT DOCUMENTS

| | | |
|---|---|---|
| CN | 103908346 A | 7/2014 |
| CN | 105232155 A | 1/2016 |
| EP | 1125557 A2 | 8/2001 |
| GB | 2537741 A | 10/2016 |
| JP | H07328016 A | 12/1995 |
| JP | 2005103091 A | 4/2005 |
| JP | 2010524548 A | 7/2010 |
| KR | 20110049703 A | 5/2011 |
| WO | WO-0030548 A1 | 6/2000 |
| WO | WO-2004002352 A2 | 1/2004 |
| WO | WO-2009045827 A2 | 4/2009 |
| WO | WO-2010093152 A1 | 8/2010 |
| WO | WO-2011060139 A2 | 5/2011 |
| WO | WO-2012158458 A2 | 11/2012 |

OTHER PUBLICATIONS

International Search Report and Written Opinion for Application No. PCT/US2017/042228, dated Nov. 28, 2017, 12 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

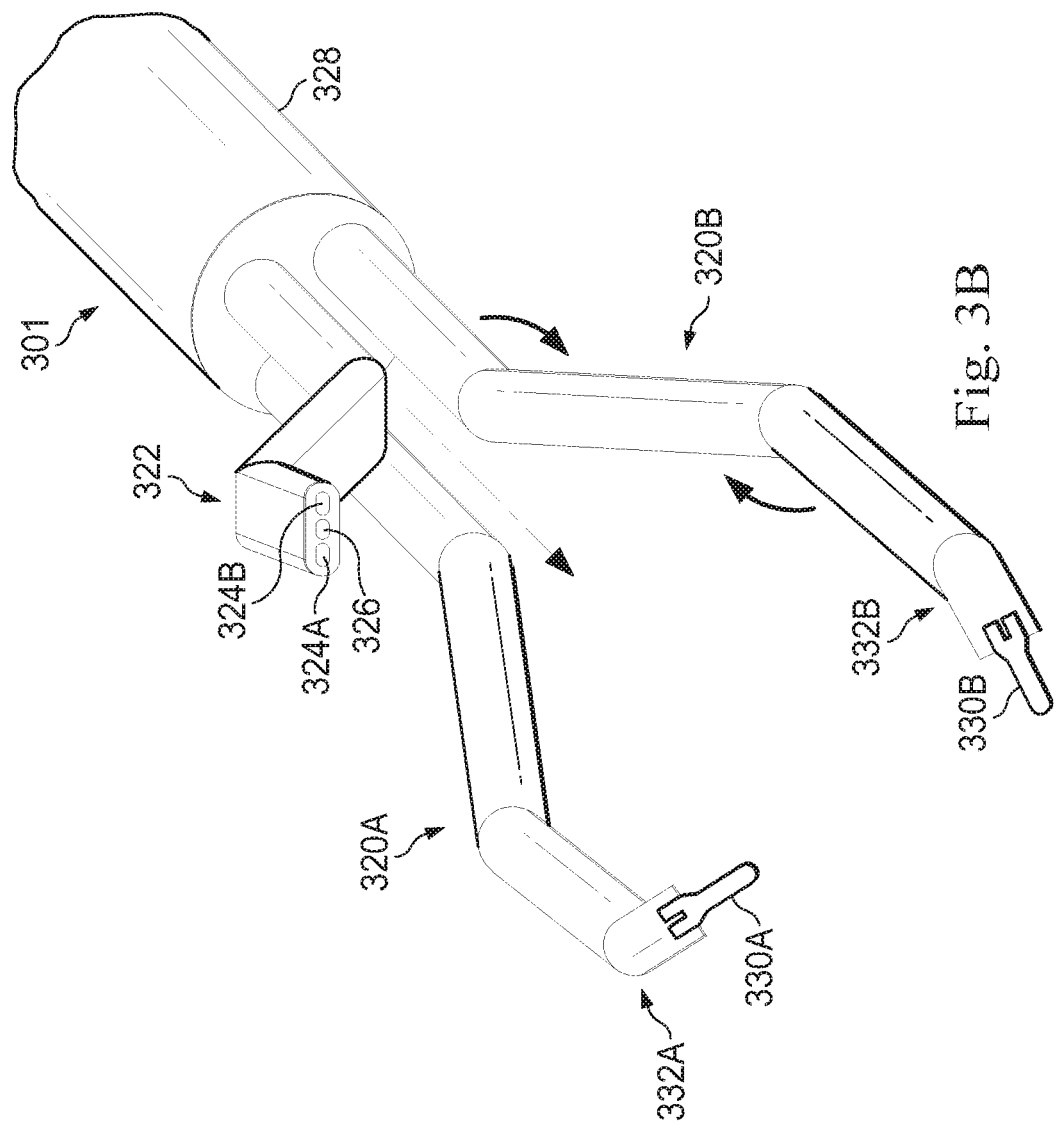

SECONDARY INSTRUMENT CONTROL IN A COMPUTER-ASSISTED TELEOPERATED SYSTEM

RELATED APPLICATIONS

This patent application is the U.S. national phase of International Application No. PCT/US2017/042228, filed Jul. 14, 2017, which designated the U.S. and claims priority to and the benefit of the filing date of U.S. Provisional Patent Application 62/362,355, entitled "Secondary Platform Instrument Control in a Computer-Assisted Teleoperated Surgical System," filed Jul. 14, 2016, all of which are incorporated by reference herein in their entirety.

TECHNICAL FIELD

The present disclosure is directed to systems and methods for controlling two or more teleoperational manipulators.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions physicians or other staff may insert minimally invasive medical instruments (including surgical, diagnostic, therapeutic, or biopsy instruments) to reach a target tissue location. To facilitate control by an operator, techniques have been used to make the control the medical instruments intuitive. However, as more instruments are involved in a given procedure and/or the instruments are not coupled to each other in a known configuration the control of all the instruments becomes more complicated. This is true as well in non-medical contexts, such as in industrial applications, in which multiple manipulators are controlled from a particular perspective.

Accordingly, it would be advantageous to provide control systems and methods that enable control of multiple instruments in changeable configurations with respect to each other.

SUMMARY

The embodiments of the invention are best summarized by the claims that follow the description.

Consistent with some embodiments, one general aspect includes One general aspect includes a teleoperational system including: a first manipulator configured to support an instrument moveable within an instrument workspace, the instrument having an instrument frame of reference, an operator input device configured to receive movement commands from an operator, and a control system configured to implement the movement commands. The control system of the teleoperational system implements the movement commands by comparing an orientation of the instrument with an orientation of a field of view of the instrument workspace to produce an orientation comparison. When the orientation comparison does not meet an orientation criterion set, the control system causes instrument motion in a first direction relative to the instrument frame of reference in response to a movement command. When the orientation comparison meets the orientation criterion set, the control system causes instrument motion in a second direction relative to the instrument frame of reference in response to the movement command, where the second direction differs from the first direction.

Consistent with other embodiments, another general aspect includes a method of controlling a teleoperational system. The method includes comparing an orientation of a manipulator arm configured to receive an instrument with an orientation of a field of view of a workspace to produce an orientation comparison. When the orientation comparison does not meet an orientation criterion set, the method includes causing instrument motion in a first direction relative to an instrument frame of reference in response to a movement command. When the orientation comparison meets the orientation criterion set, the method includes causing instrument motion in a second direction relative to the instrument frame of reference in response to the movement command, where the second direction differs from the first direction. Other embodiments of this aspect include corresponding computer systems, apparatus, and computer programs recorded on one or more computer storage devices, each configured to perform the actions of the methods.

Consistent with other embodiments, another general aspect includes a robotic system. The robotic system includes an operator input system having a first input device, a first robotic platform having a first slave manipulator arm configured to receive a first instrument. The first slave manipulator arm and the first instrument have at least one reference frame. The robotic system also includes a second robotic platform having a second slave manipulator arm configured to receive an imaging system, where the imaging system provides an imaging reference frame, and a control system that receives movement commands via the first input device. The received movement commands indicate a first direction of movement relative to the imaging reference frame. The control system implements the received movement commands on a platform of the first and second robotic platforms by comparing an orientation of the first instrument in the instrument reference frame with an orientation of the imaging system in the imaging reference frame, determining a mapping to apply to the received movement commands to generate implementable movement commands for the first instrument, and causing instrument motion in a second direction relative to the instrument reference frame in response to the movement command, where the second direction is different than the first direction.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 3B is a simplified diagram of a distal end of a bundled unit of medical devices according to some aspects of the present disclosure.

Figure 1:
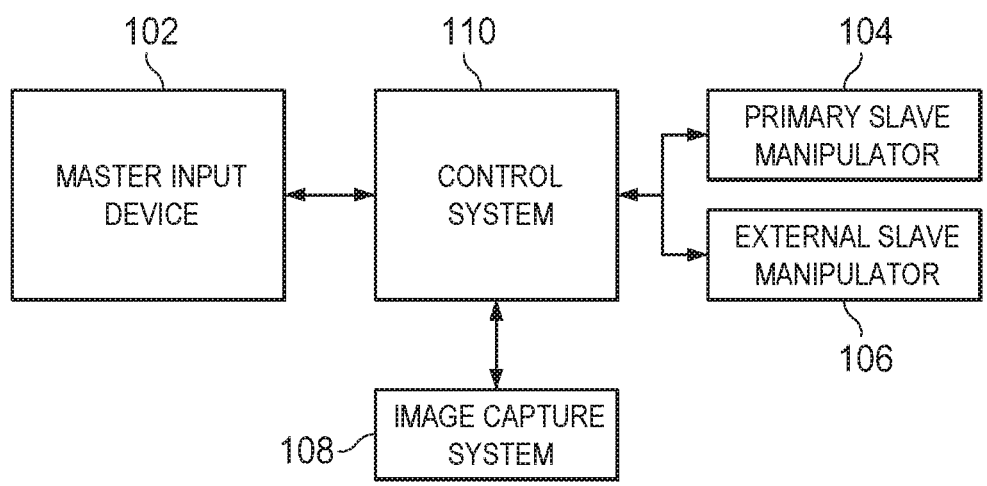
FIG. 1 is a diagrammatic view showing general system components of a computer-assisted, teleoperated system, according to some aspects of the present disclosure.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their position, orientation, and/or pose in three-dimensional space. As used herein, the term "position" refers to the location of an object or a portion of an object in a three-dimensional space (e.g., three degrees of translational freedom along Cartesian X, Y, and Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom).

While some embodiments provided herein are discussed primarily with respect to medical procedures, any reference to medical or surgical instruments and medical or surgical methods is non-limiting. The systems, instruments, and methods described herein may be used for animals, human cadavers, animal cadavers, human or animal tissue removed from human or animal anatomy and not to be returned to such human or animal anatomy, non-surgical treatment, diagnosis, or cosmetic improvements. The systems, instruments, and methods described herein may also be used for industrial systems and general robotic or teleoperational systems, including those for manipulating or otherwise interacting with work pieces not comprising human or animal tissue.

FIG. 1 is a diagrammatic view that shows general system components of a computer-assisted, teleoperated system 100. As shown, the system includes a primary slave manipulator 104 that moves and controls a first instrument, and an external slave manipulator 106 that moves and controls a second instrument. Such manipulators are also called arms or manipulator arms. When implemented as a medical system, the instruments of the system 100 may be referred to as medical instruments. The system 100 includes a control system 110 and at least one input device 102 (sometimes also called a "master tool manipulator," "MTM," "master input device," or "master device") that receives inputs from an operator. The control system 110 receives the inputs as electronic signals and generates corresponding movement commands that are implemented by the control system 110 to move and control the slave manipulators 104 and 106 and any associated instruments. The system includes an image capture system 108 that captures video images of an operational site or work site, such as a surgical site in medical implementations. The image capture system 108 optionally includes an image system slave manipulator and camera instrument, including an imaging sensor such as a CCD or CMOS or ultrasonic or fluoroscopic image sensor, that is moved and operated by the image system slave manipulator to change the field of view provided by the camera instrument.

As described, motion of the primary and external slave manipulators, and of the image capture system manipulator and camera instrument, is under teleoperated control corresponding to movement of part or all of the input device 102. One or more hand-held or hand-grasped input control devices may enable the input device 102 to permit an operator (e.g., a surgeon, a clinician, or a physician) to control teleoperational slave manipulators 104 and 106 and, in some embodiments, to view the work site.

The input device 102 may be an untethered remote-control type device that communicates wirelessly. Alternatively, the input device 102 may be a control device tethered electrically with one or more cables, tethered mechanically via one or more mechanical links or other structure, or tethered both electrically and mechanically. The input device 102 may also be optionally tethered, such as be an input device capable of operating wirelessly and under its own power as well as attached to electrical cables or mechanical structures. As a specific example, the input device 102 may be disposed at or as part of an operator's console. An example of an operator console 200 (sometimes called a "surgeon console" if the operator console is primarily used by a surgeon) including one or more related input mechanisms, that may provide the input device 102, is included in FIG. 2.

Figure 2:
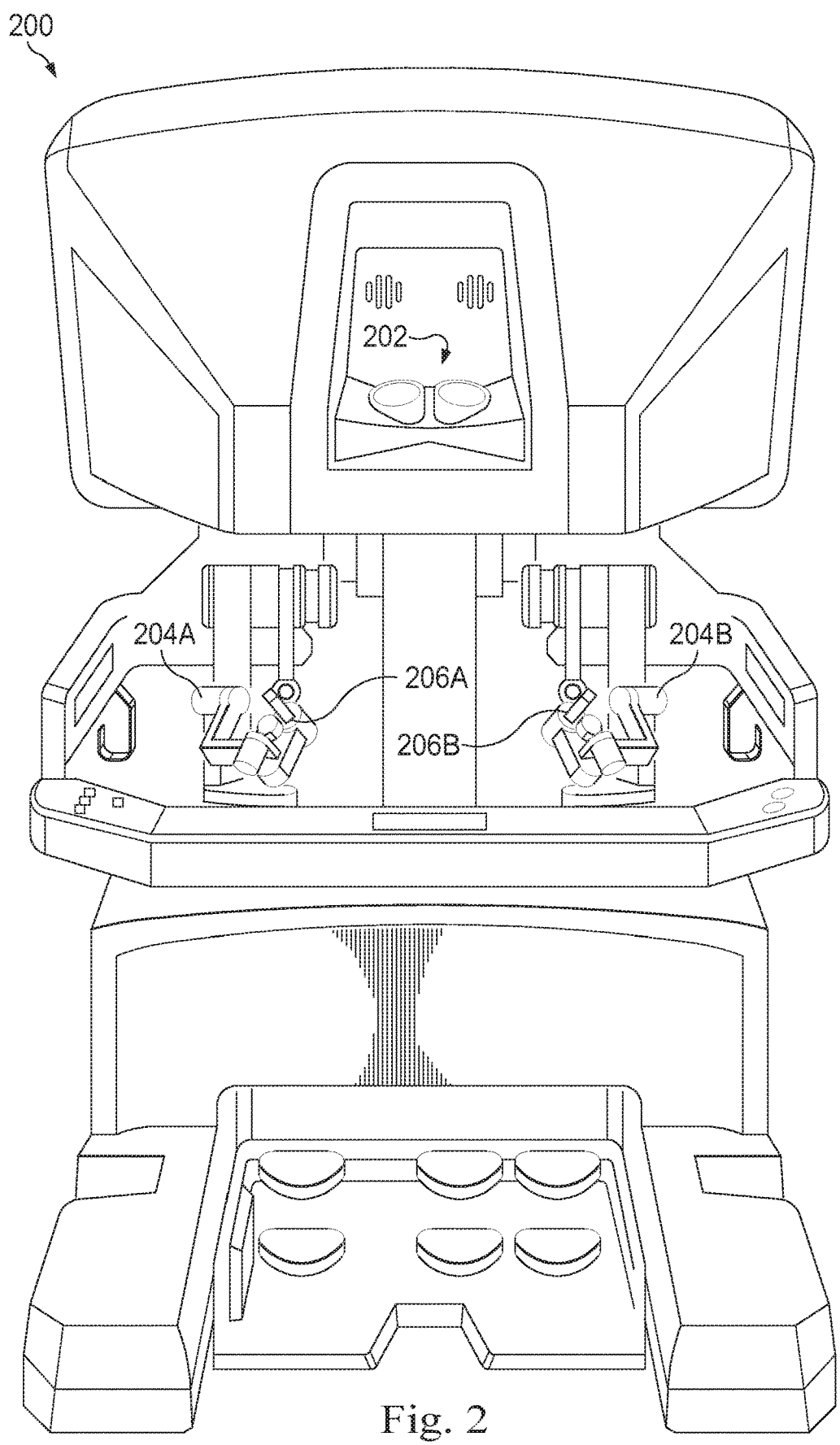
FIG. 2 is a front elevation view of an operator console for controlling a computer-assisted teleoperated system, such as the teleoperated system of FIG. 1, according to some other aspects of the present disclosure.

FIG. 2 is a front elevation view of an operator console 200, similar to a "surgeon" console of a da Vinci® Surgical System commercialized by Intuitive Surgical, Inc. of Sunnyvale, Calif. At the master control console, an operator views video images captured by the image capture system 108. The video may be displayed in a display system 202, which, as shown, includes two separate viewers or displays that align with the eyes of the operator during operation. The display system 202 may provide stereoscopic views from the image capture system 108 to enable the operator to perceive the field-of-view of the image capture system 108 in three dimensions. The three-dimensional view from the image capture system 108 may permit the operator to better interact with the environment shown in the display system 202, such as by manipulating structures in the environment. Other display system configurations may be used as the display system 202, in other embodiments.

The operator console 200 includes one or more input device 204 (two are shown as input device 204A and input device 204B). The exemplary input devices 204 may each include a shaft configured to be positioned by at least two fingers of the operator's hand. The input devices 204 may be coupled to console 200 by kinematic linkages. As the operator moves a input device 204 within the range of motion permitted by the operator console 200, the control system 110 interprets the movements as commands that can be used to control the slave manipulators 104 and 106 to cause them to make corresponding movements. Additionally, the input devices 204 include a plurality of linked members, linked together by rotational joints, each joint having at least one encoder. Similarly the shafts 206 may be rotationally coupled to the input device 204 to provide additional input means. For example, rotating one of the shaft 206A or 206B may cause a corresponding rotational movement of an instrument end effector disposed on or integrated into one of the slave manipulators 104 or 106. In some embodiments, rotation of the shafts 206 may result in other operations. The shafts 206 may include buttons or other input means, in some embodiments.

Embodiments of the input devices 204 may include or further include any number of a variety of input devices, such as joysticks, trackballs, data gloves, trigger-guns, hand-operated controllers, voice recognition devices, body motion or presence sensors, and/or the like. To provide an operator with a strong sense of directly controlling manipulators 104 and 106, the input devices may be provided with the same degrees of freedom as the associated manipulators 104 and 106. In this manner, the input devices provide the operator with telepresence or the perception that the input devices, e.g. the input devices 204, are integral with slave manipulators 104 and 106. In some embodiments, the input devices 204 may have more or fewer degrees of freedom than the associated slave manipulators 104 or 106 and still provide the operator with telepresence. In some embodiments, the input devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Changes in the position of the input device 204 and the orientation of the input devices 204 and the shafts 206 may be interpreted by the control system 110 and used to produce movement commands. The control system 110 may implement such commands, causing the slave manipulators 104 and 106 to move as directed by the operator through the input devices 204. The operator console 200 may include all or part of the control system 110, or the control system 110 may be located elsewhere. The control system 110 includes one or more processing devices and memory for storing programmatic instructions and data that can be executed and processed by the one or more processing devices. The operator console 200 optionally includes one or more foot pedals (seven are shown in FIG. 2) and other user input mechanism, such as switches on the armrest or on the individual master manipulators grasped with the fingers.

As is discussed herein, in some aspects of the disclosure, the field of view of the camera instrument of the image capture system 108 is oriented toward a work site, and a secondary instrument (which may be controlled by a primary platform or controlled by a secondary platform) is oriented so that the direction of insertion is toward the image capture system 108. In one implementation, the secondary instrument being inserted toward the camera instrument means the secondary instrument has an insertion direction with a component antiparallel to a viewing direction (also called "line of sight") along the central axis of the camera instrument's field of view. In another implementation, the secondary instrument being inserted toward the camera instrument means the secondary instrument has a component of a particular magnitude (larger than a threshold magnitude) antiparallel to the viewing direction along the central axis of the camera instrument's field of view; this magnitude may be normalized as a ratio of: (1) component antiparallel to the central axis of the camera instrument's field of view to (2) component perpendicular to the central axis of the camera instrument's field of view.

In some implementation, the secondary instrument being inserted toward the camera instrument means the secondary instrument has an insertion direction with an angular difference of a certain amount relative to a viewing direction of the camera instrument. For example, in some implementations, the secondary instrument is identified as having an insertion direction toward the camera instrument when the angular difference is equal or greater than 90 degrees, 120 degrees, 135 degrees, etc.

In some embodiments, the tips of the camera instrument and the secondary instrument may be positioned such that a plane can be envisioned between the tips of these instruments with the plane being perpendicular to a central axis of the field of view of the camera instrument. In terms of this plane, one way to think about the relative insertion directions is that the camera instrument is located on one side of the plane, and the secondary instrument controlled by the secondary arm enters the operational site on the opposite side of the plane.

Figure 3A:
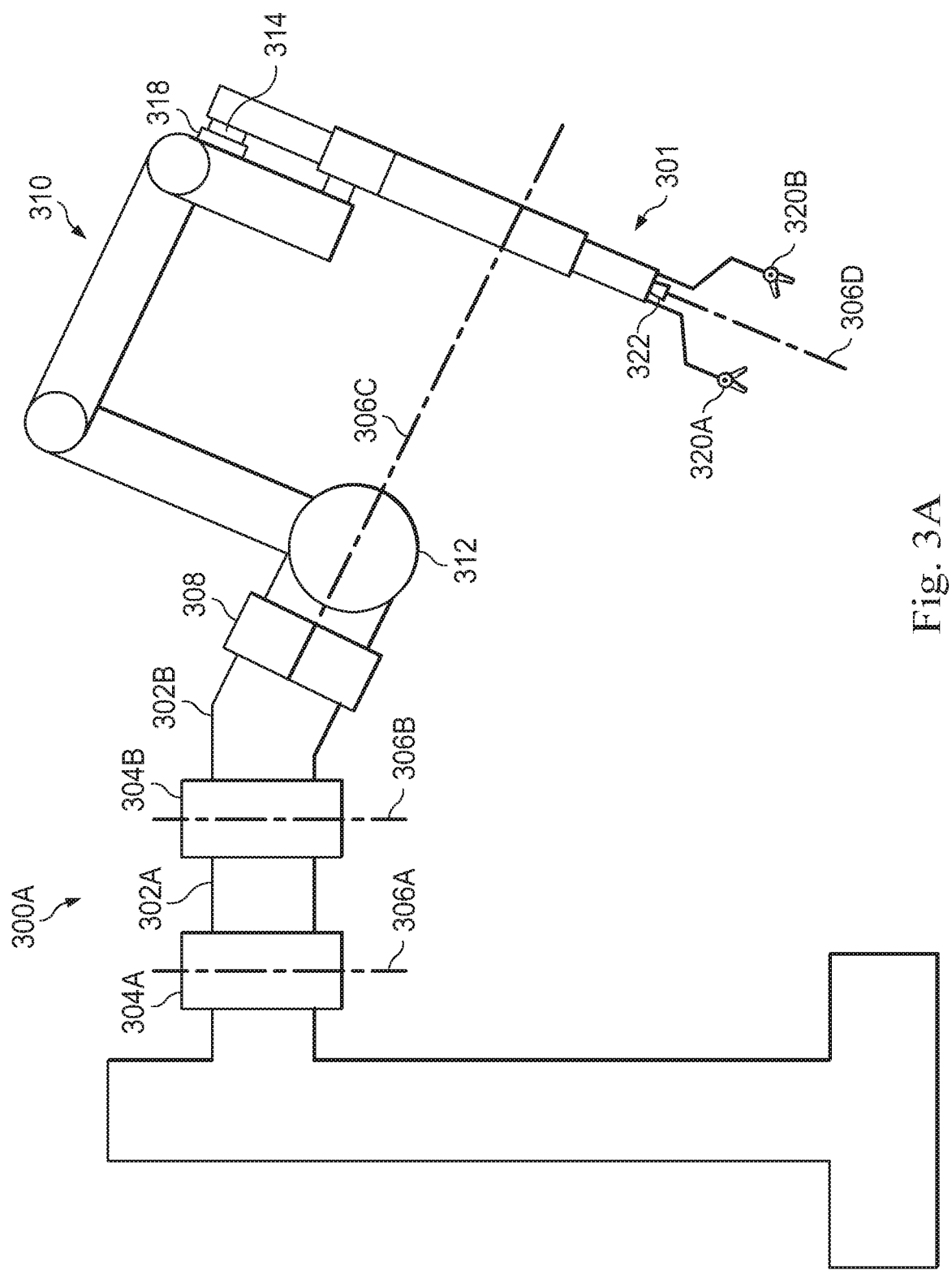
FIG. 3A illustrates a front elevation view of aspects of an exemplary teleoperational assembly according to embodiments of the present disclosure.

FIG. 3A is a simplified side view (not necessarily to scale or complete) of some embodiments of the slave manipulators 104 and/or 106, referred to as teleoperational arm assembly 300A. The teleoperational arm assembly 300A is depicted as holding a bundled unit 301 of medical devices. The bundled unit 301 may then be inserted into the patient P through an incision and through a tool guide. The teleoperational arm assembly 300A is mechanically supported by a base B. Links 302A and 302B (generally, links 302) are coupled together and to the base B through horizontal setup joints 304A and 304B (generally, setup joints 304). The setup joints 304 in the depicted example are passive joints that allow manual positioning of the assembly 300A when their brakes are released; in other embodiments, they may be active joints that can be controlled via operator input. As depicted, setup joint 304A allows link 302A to be manually rotated about axis 306A, and setup joint 304B allows link 302B to be manually rotated about axis 306B. Although only two links and two setup joints are shown in this example, more or fewer of each may be used as appropriate in this and other teleoperational arm assemblies in conjunction with the present invention.

The teleoperational arm assembly 300A also includes two active joints and transmission system (which can comprise a number of gears or pulleys or cables or belts or other transmission components) driven by motors. A yaw joint 308 allows arm section 310 (which may include a linkage of multiple arm segments) to rotate around an axis 206C, and a pitch joint 312 allows arm section 310 to rotate about an axis perpendicular to that of axis 306C and orthogonal to the plane of the drawing. An interface 314 comprises mating parts on the carriage 316 and the proximal end of the bundled unit 301 such as motor driven gears that actuate movement of instruments 320A and 320B (also called tools 320A and 320B, and generally called instruments 320) and an image capturing system 322 through conventional joints, cable and pulley systems. In addition, the bundled unit 301 is coupled to a carriage 318 on the arm section 230 which in turn is coupled to a linear drive mechanism to extend or retract the bundled unit 301 along its insertion axis 306D.

Although each of the yaw joint 308, pitch joint 312 and motor driven gears in the carriage 318 may be controlled by an individual joint or gear controller, the controllers may be controlled by a common master/slave control system so that the devices of the bundled unit 301 may be controlled through operator manipulation of its associated control device, such as one or both of the input devices 204 of FIG. 2.

Referring now to FIG. 3B, shown therein is a perspective view of a distal end of the bundled unit 301. As illustrated, the bundled unit 301 includes instruments 320 that are removable medical tools for performing a medical procedure, and a removable image capturing system 322 for viewing the procedure at a surgical site within a patient. Each of the instruments 320 and image capturing system 322 extends through a separate lumen formed in an inner core of the bundled unit 300. Replacement of one or both of the instruments 320 during or in preparation for performing a medical procedure may then be accomplished by removing the tool that is no longer needed from its lumen and replacing it with a substitute tool or instrument by inserting the substitute tool in the vacated lumen. Alternatively, if unused lumens are available, an additional tool may be inserted through one of those available lumens without removing any other tools already in place.

The image capturing system 322, as shown in FIG. 3B, includes a stereoscopic pair of cameras 324A and 324B (and/or a single monocular or binocular camera) for three-dimensional imaging of the surgical site and an illuminating device 326 such as a light emitting diode (LED) or a fiber optics bundle carrying light from an external source, to enhance visibility of objects in the captured images. Auxiliary image capturing units, such as an ultrasound probe or another optical camera, may also be provided in available lumens of the bundled unit 301 for "seeing" into structures, such as anatomic structures for surgical or diagnostic purposes.

In some embodiments, an overtube 328 is also included in the bundled unit 301 for protecting its inner core and the medical devices (i.e., surgical tools and image capturing units) inserted therethrough. The overtube 328 may be rigid. Alternatively, it may be formed of flexible material or comprise actively and/or passively bendable sections so that the bundled unit 301 may conform to the shapes of body lumens as it moves therethrough to a surgical site within a patient.

The instruments 320 each have a controllably extendable, rotatable, and bendable shaft to which their respective end effectors 330A and 330B are coupled to by wrist mechanisms 332A and 332B, respectively. In the depicted embodiment, the shaft of the instrument 320B comprises three links coupled by distal joints. The most proximal link (the "proximal first link") of the three links is controllably extendable and retractable along an insertion axis, which may be parallel to the insertion axis 306D of the bundled unit 301), and is controllably rotatable about the insertion axis. The middle second link, on the other hand, may be controllably bendable by a distal joint relative to the proximal first link, and the most distal link (the "distal third link") is coupled to the first and second links and bendable by distal joint so that its bend angle is in an opposite direction as that of the middle second link and consequently, keeps distal third link and the proximal first link in parallel alignment.

The shaft of the instrument 320A is similarly constructed as that of the instrument 320B. Additional details for one example of the wrist mechanisms 332A and 332B are provided in commonly owned U.S. Pat. No. 6,817,974 "Surgical Tool Having Positively Positionable Tendon-Actuated Multi-Disk Wrist Joint."

The image capturing system 322 may also have a controllably extendable, rotatable, and bendable shaft that facilitates at least insertion/retraction of the image capturing system 322 along its insertion axis (which may be parallel to the insertion axis 306D of the bundled unit 301), and that facilitates pitch motion in order to achieve a sufficient elevation of the image capturing system 322 "above" the instruments 320 so as to properly view them during a surgical procedure. Additional degrees of freedom, such as roll angular movement of the image capturing system 322 about its insertion axis, may also be provided in order to facilitate additional positioning and orientation capabilities for the image capturing system 322. For enhanced maneuverability, the shaft of the image capturing system 322 may also be bendable such as the controllably bendable, rotatable, and extendable shaft of the instruments 320.

Figure 3C:
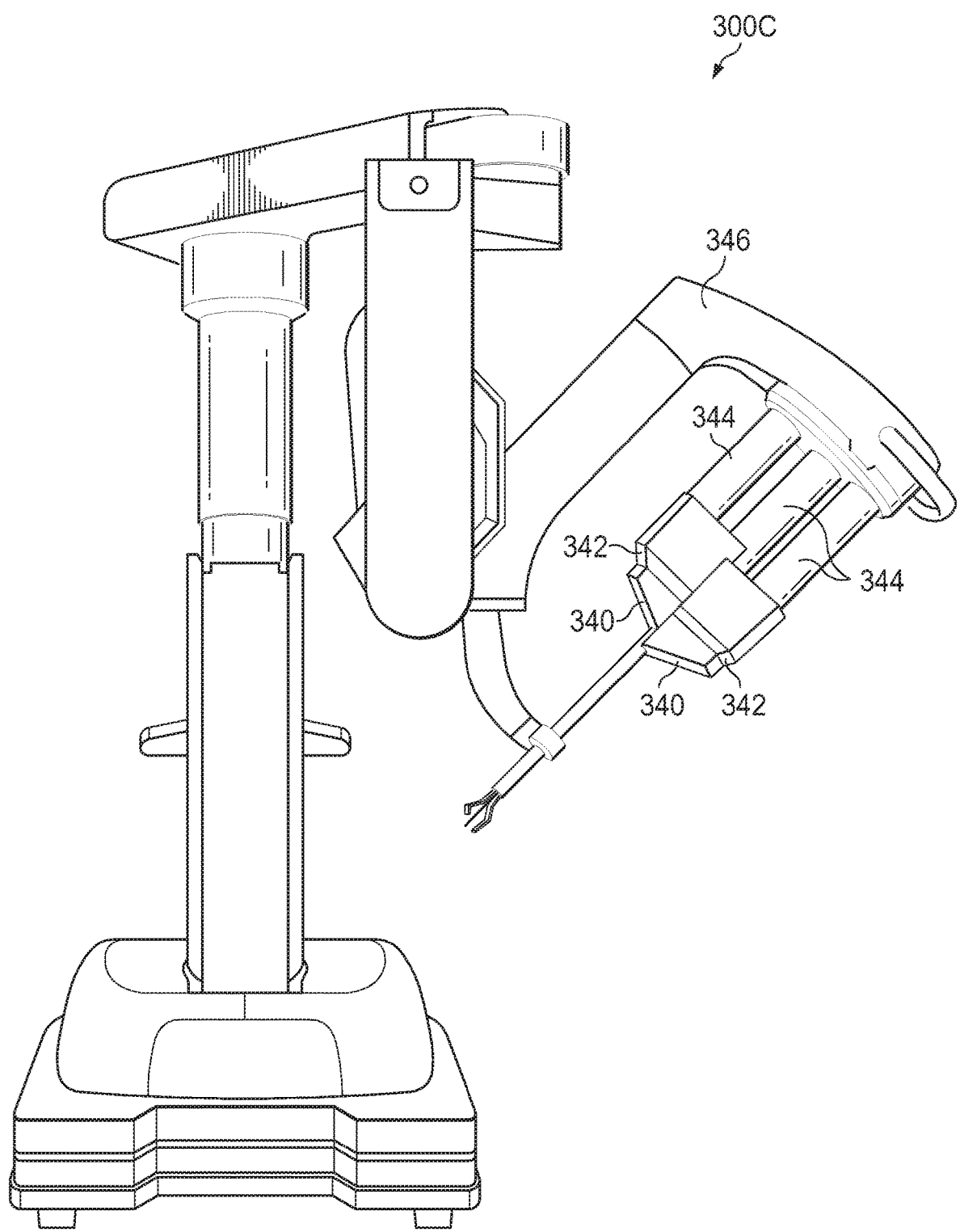
FIG. 3C is a perspective view of the teleoperational assembly of FIG. 3A according to some aspects of the present disclosure.

FIG. 3C is a perspective view of one embodiment of a teleoperated system 300C, according to some aspects of the present invention. The depicted embodiment of FIG. 3C shows an example of a system 300C including replaceable medical instruments 340 that may contain release mechanisms such as disclosed herein. System 300C, which may, for example, include a da Vinci® Surgical System commercialized by Intuitive Surgical, Inc., employs multiple surgical instruments 340, each of which is mounted in an instrument mount 342 on a manipulator arm 344 of a robotic system 346. A sterile barrier (not shown in FIG. 3C) including a drape and instrument adaptors may be between a patient (not shown) and robotic system 346 in medical applications. Instruments 340 may vary in structure and purpose but may still be interchangeable, so that a user can select and mount various instruments 340 in instrument mounts 342 of robotic system 346 as needed for a particular medical procedure and can swap instruments 340 during a medical procedure to provide desired clinical functions. Each instrument 340 generally includes an end effector or distal tool tip, an instrument shaft, and a backend. As described herein, different instruments 340 may have many different shapes or sizes and may include forceps, graspers, scalpels, scissors, cautery or ablation tools, or needle drivers to name a few possibilities. Instruments 340 having different distal tool tips may be mounted on different manipulator arms 344 of robotic system 346 and may work cooperatively at the same work site. An endoscopic camera, for example, a stereoscopic camera, can also be mounted on a manipulator arm to provide visual information, particularly images of the work site in which distal tool tips of instruments 340 may be operating. The instrument mounts 342 of robotic system 346 may include actuators such as drive motors that provide mechanical power to actuate mechanical structures in instruments 340 via drive couplings that connect the actuators through an interface mechanism to inputs of instruments 340.

Figure 3D:
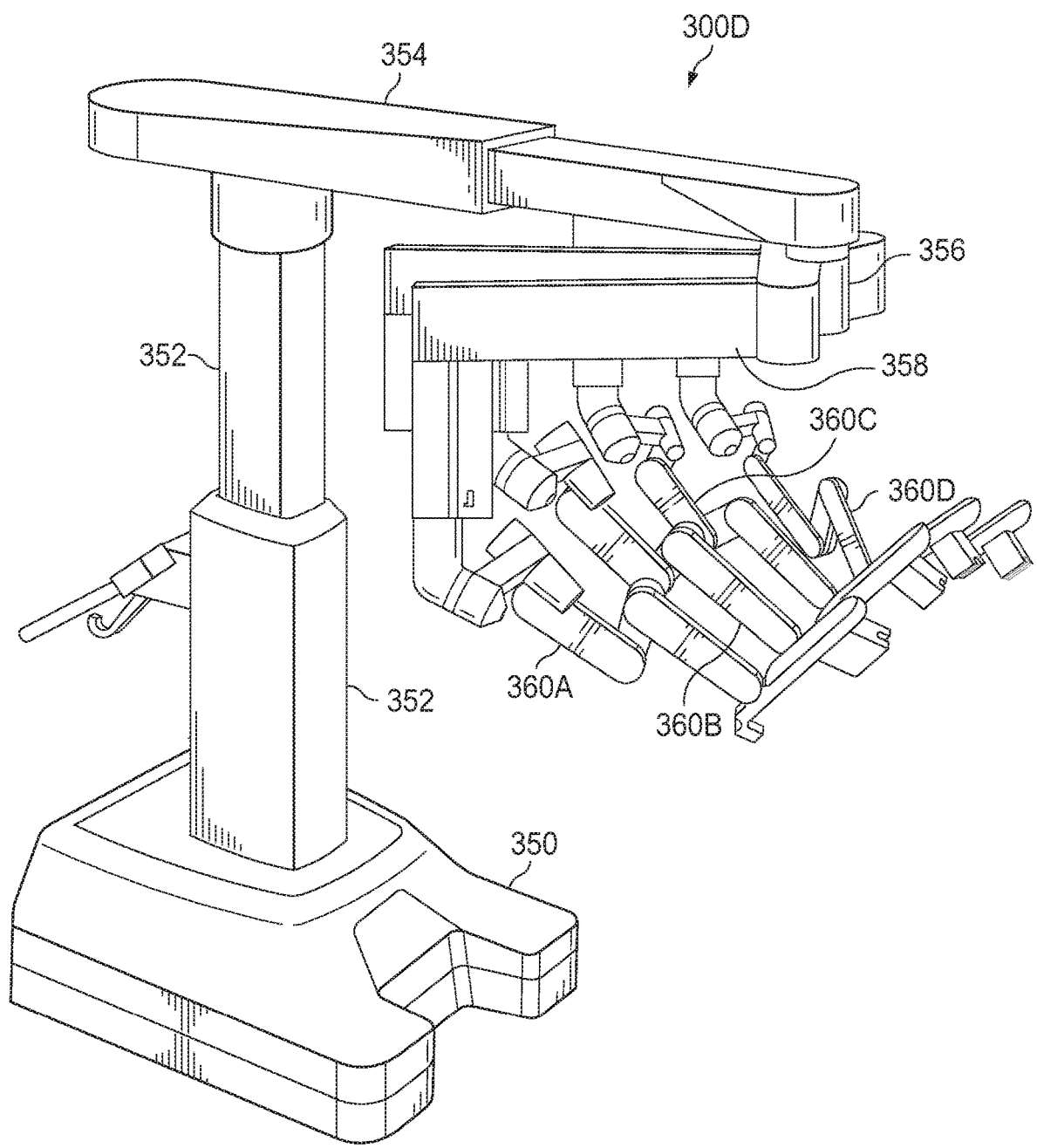
FIG. 3D is a perspective view of an exemplary teleoperational assembly having a plurality of manipulator arms, according to some aspects of the present disclosure.

FIG. 3D depicts another embodiment of a teleoperated assembly 300D, which includes multiple manipulator arms supported by a column extending from a base. The assembly 300D includes an automated and motorized setup structure that supports projecting manipulator arms, and may include a base 350 that rests on the floor, a telescoping support column 352 that is mounted on the base, a telescoping boom 354 that extends from the support column 352, and an orienting portion as an orienting platform 356. The assembly 300D also includes support beams 358, and several manipulator arms 360 that support surgical tools including portions of the image capture system 108 of FIG. 1. As shown in FIG. 3C, manipulator arms 360A, 360B, 360C, 360D are instrument arms that support and move the instruments, such as medical instruments used to manipulate tissue. One of these manipulator arms 360 may be designated as a camera arm that supports and moves a camera instrument. The camera system may be a stereo endoscope for capturing stereo images of the surgical site and providing the separate stereo images to the display system 202 of FIG. 2. Other implementations of the imaging system are discussed herein.

Knowledgeable persons will appreciate that the manipulator arms that support the instruments and the camera may also be supported by the base 350 or another base, such as a platform (fixed or moveable) mounted to a ceiling or wall, or in some instances to another piece of equipment in the operating room (e.g., an operating table). Likewise, they will appreciate that two or more physically separate bases may be used (e.g., one base supporting one arm).

Figure 3E:
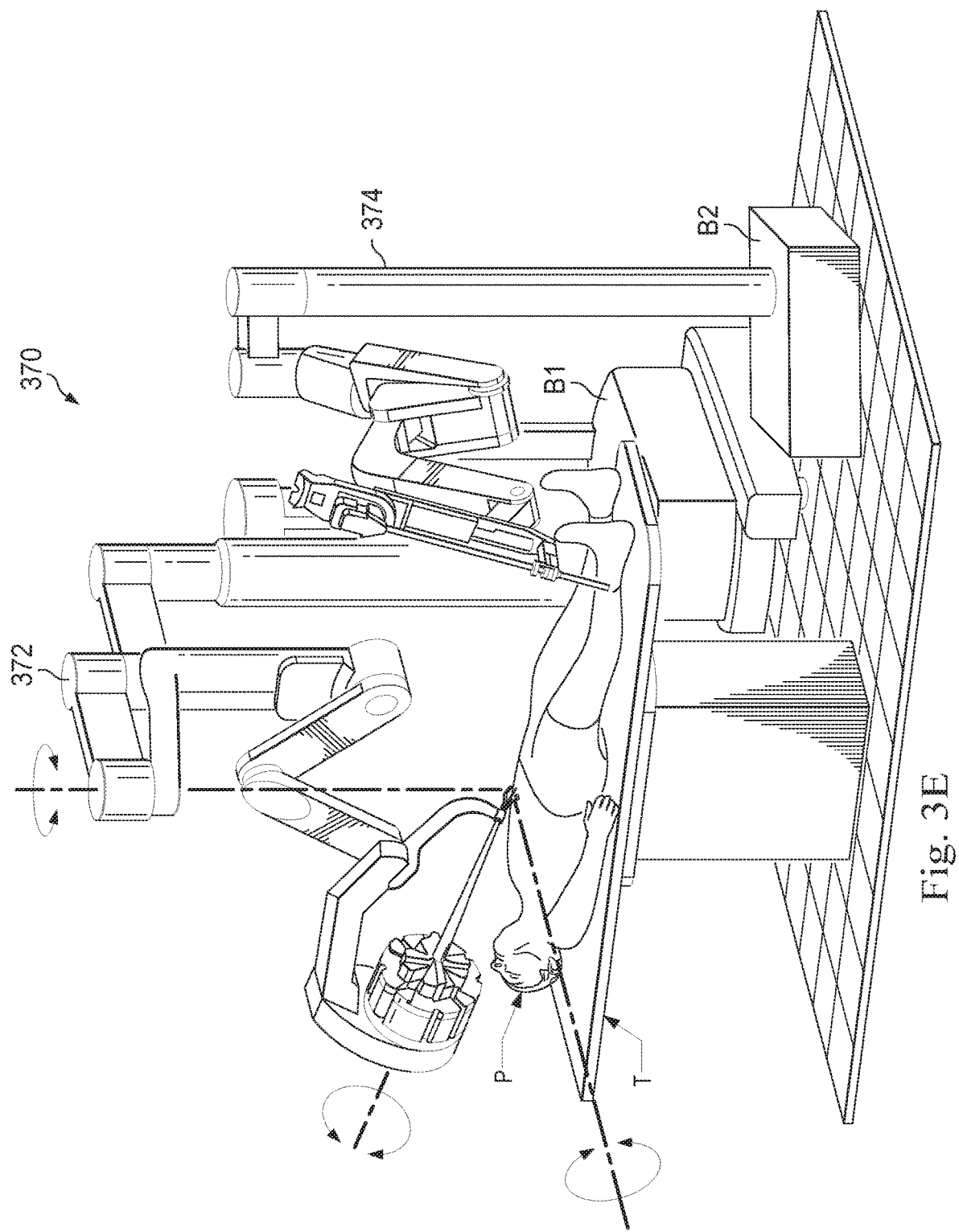
FIG. 3E is a perspective view of a computer-assisted teleoperated medical system including two platforms, according to some aspects of the present disclosure.
Figure 3F:
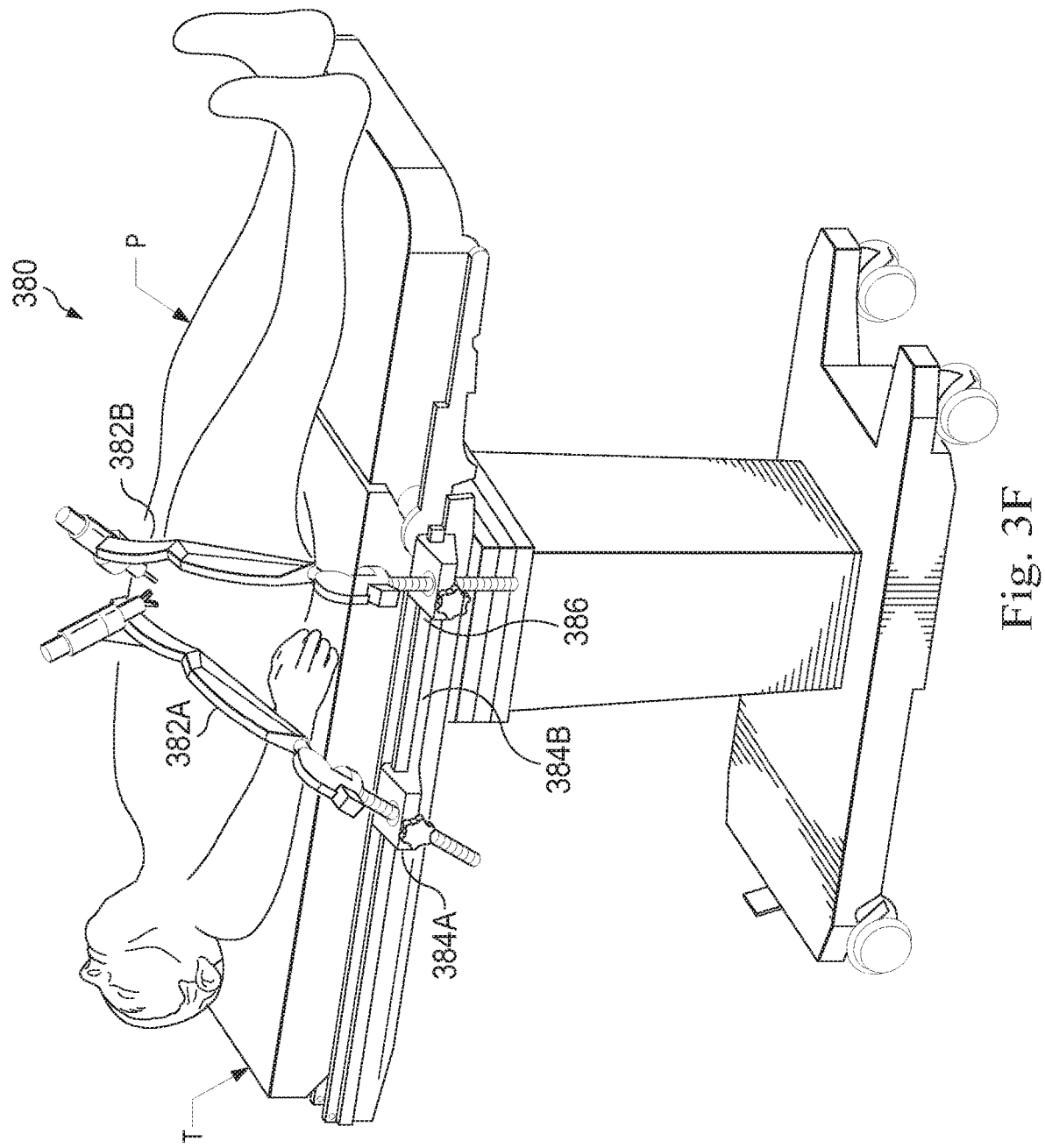
FIG. 3F is a perspective view of another computer-assisted teleoperated medical system including two platforms, according to some other aspects of the present disclosure.

FIGS. 3E and 3F depict embodiments of manipulator assemblies with different platforms. FIG. 3E is a perspective view of a computer-assisted teleoperated medical system 370 that includes two major components (platforms) that interact with a patient. System 370 includes a primary teleoperated platform 372 (also called primary teleoperated assembly 372) that includes several medical instruments and a camera instrument like the assembly 300A of FIG. 3A, system 300C of FIG. 3C, or assembly 300D of FIG. 3D. For clarity, FIG. 3E includes a depiction of system 300C of FIG. 3C as the platform 372, which includes a single manipulator arm. However, other embodiments may include additional manipulator arms, as in assembly 300D of FIG. 3D. These manipulator arms may each be individually operated by an associated manipulator, such as one of the input devices 204 (FIG. 2) to perform medical tasks at a work site in the patient P, positioned on the table T. U.S. Pat. No. 7,955,322, filed Dec. 20, 2006 and entitled "Wireless Communication in a Robotic Surgical System," depicts some examples of a primary teleoperated platform and is incorporated herein by reference in its entirety.

System 370 also includes a secondary teleoperated platform 374 that may include one or more instruments, each individually operated by an associated manipulator, such as one of the input devices 204 (FIG. 2). In use, the secondary teleoperated surgical platform 374 controls one or more instruments at the surgical site. The secondary teleoperated platform 374 may optionally be referred to as being external to the primary teleoperated platform 372. As shown, each of the primary and secondary platforms is mounted on an individual base, like the base B1 and the base B2. The assemblies or platforms may comprise or be mounted to separately movable carts, in some embodiments, so that they can be independently positioned within an operating room or other work environment. In other optional implementations, however, the secondary platform may be located in various other ways, such as permanently fixed to a mechanical ground (such as a floor, ceiling, or wall), permanently or removably mounted to the operating table, or permanently or removably mounted to the primary platform.

As another example, FIG. 3F is a perspective view of another embodiment of a computer-assisted teleoperated system 380. A wheeled table T having a table surface is positioned on the table base. The table surface can be used to support a work piece such as the patient P or a non-human work piece in other applications. In the example shown in FIG. 3F, two slave manipulator arms 382A and 382B are positioned for operation on the patient P. The arms 382A and 382B are supported by arm platforms 384A and 384B that may be removably and repositionably attached to a number of different locations along a table rail 386. During operation, the controllable arms 382A and 382B are driven to position tools and instruments. For example, the instrument 388A may be an imaging system and the instrument 388B may be a pair of forceps for positioning tissue. In some implementations, the controllable arms 382A and 382B are teleoperable and include remotely operable powered joints that, when driven, reposition and reorient the tools.

Both FIGS. 3E and 3F show configurations in which a manipulator arm and supported instrument on one platform (a primary instrument on a primary platform) may approach a work site from a substantially different side or direction from which an arm and supported instrument on another platform (a secondary instrument on a secondary platform) approaches the work site. For example, while the camera instrument may define a field of view, other instruments may approach the work site from different sides of a plane associated with the field of view. Such a configuration can pose problems for providing intuitive control to an operator that is able to control the arms approaching the site from different sides using a single console, like the console 200 of FIG. 2.

Figure 4A:
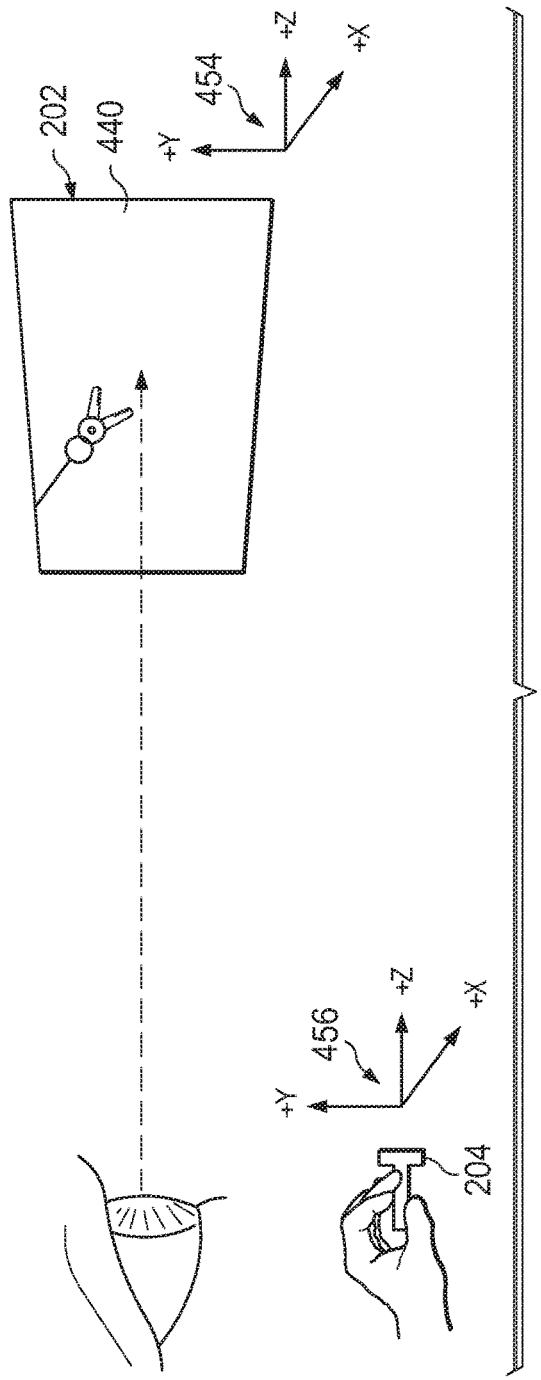
FIG. 4A is a diagrammatic view of some system components and associated frames of reference from the operator side of the system, according to some embodiments of the present disclosure.
Figure 4B:
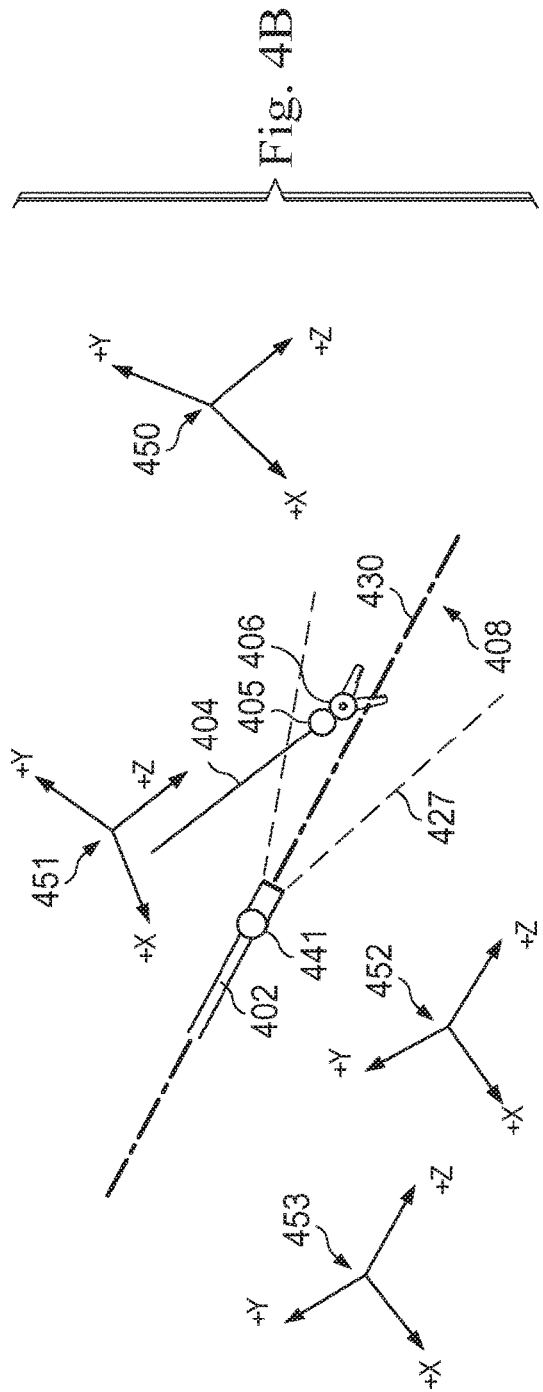
FIG. 4B is a diagrammatic view of some system components and associated frames of reference from the instrument side of the system, according to some embodiments of the present disclosure.

FIGS. 4A-4B are diagrammatic view of some system components and associated Cartesian frames of reference. FIG. 4A shows portions from the operator side of the system. FIG. 4B shows portions from the instrument side of the system. Frames of reference are also often called "reference frames." Also, frames of reference as discussed in this application are used to explain the different orientations, locations, rotational differences or changes, and translational differences and changes associated with the techniques discussed herein, along with the associated mappings for determining relative locations and orientations, input, and motion commands. Some embodiments implementing the described techniques need not use the exact same reference frames in calculations or in operating the system. For example, the axes of a reference frame may be set differently from what is described in detail in this disclosure. Also, in implementations that use only orientation, the reference frames may only rotate and not translate. Further, other systems may use alternate coordinate systems, such as spherical coordinate systems.

As shown in FIG. 4B, the imaging system 402 has a field of view 427. A work piece 430 and a distal portion of instrument 404 are positioned within the field of view 427. In this example, the instrument 404 includes a joint 405 and an end effector 406. A reference frame 450 has been noted for the shaft of the instrument 404, proximal to the joint 405, and with insertion of the instrument 404 defined as the +Z direction in reference frame 450. The reference frame 450 translates and rotates with the translation and rotation of the instrument 404. A reference frame 451 has also been noted for the end effector 406, and moves with the end effector 406. If the end effector 406 of the instrument 404 does not move with respect to the shaft of the instrument 404, such as with rigid instruments having no degree of freedom between the shaft and the end effector, then the reference frames 450 and 451 can be combined into a single reference frame that describes the position and orientation of the relevant portion of the instrument 404 for modeling and/or control.

The field of view 427 itself is associated with a reference frame 452, which translates and rotates with the field of view 427. In this example shown, movement of the field of view 427 is possible through movement of a joint or other degree of freedom 441 between shaft and distal end of the imaging system 402. Thus, FIG. 4B also shows a shaft-based reference frame 453 that translates and rotates with the proximal body of the imaging system 402. If the field of view 427 does not move with respect to the proximal body of the imaging system 402, such as when imaging system has no compliance or other degree of freedom between the field of view and the proximal body, then the reference frames 452 and 453 can be combined into a single reference frame that describes the position and orientation of the relevant portion of the imaging system 402 (such as its field of view 427) for modeling and/or control.

Where the physical dimensions of the instrument 404 and imaging system 402 are known, and where the configuration of their links and joints (e.g. joint angles for rotational joints, linear position for prismatic joints, etc.), can be assumed or determined (e.g. using position or velocity encoders, orientation or position or shape sensors, direct rotation sensors, motor position sensors, etc.), the kinematic relationship between reference frame 450 or 451 and a reference frame of any other link in the instrument 404 can be determined using well-known kinematic calculations. Likewise, the kinematic relationship between reference frame 152 or 153 and any other link in the imaging system 402. The end effector 406 operates within the field of view 427, so mapping between the reference frames 450 of the end effector 406 and the reference frame 452 of the field of view 427 will allow control of the end effector 406 in the field of view 427.

FIG. 4A further shows an operator viewing the display system 202 and grasping a master input device 204, as shown in FIG. 2. The display system 202 presents images captured by the imaging system 402 of the field of view 427. In some implementations, the display system 202 presents the images as captured, without rotation, panning, zooming, or other manipulation of the images; in this case, a direct, identity mapping can be made between the displayed image and the field of view 427's reference frame 452. In some implementations, the display system 202 presents manipulated versions of the images (e.g. rotated by 180 degrees, zoomed and panned to a particular part of the field of view, skewed, etc.); in this case, the mapping between the displayed image and the field of view 427's reference frame 452 takes into account the transformations associated with the manipulation of the image. During operation, the operator views the instrument 404's position and orientation changes on the display system 202, and establishes a relation between reference frames 454 and 456. Thus, in some implementations, the operator reference frame is a separate frame that links the reference frames 456 and 454. For example, the operator reference frame may be a reference frame based on the eyes, head, torso, other body part, etc. of the operator. As another example, the operator reference frame may be a reference frame based on a console attached to the master input device 204. In some implementations, the operator reference frame is collocated and identical to the reference frame 454, and is essentially the reference frame 454.

As shown in FIG. 4A, an image 440 of the end effector 406 is shown on the display system 202. A reference frame 454 is associated with display system 202, and a reference frame 456 is associated with master input device 204. As the master input device 204 is translated and rotated in 3D space, its associated reference frame 456 translates and rotates correspondingly relative to the operator reference frame. These translations and rotations of the master input device 204 can be sensed or otherwise determined, and thus its reference frame 456 can be translated and rotated appropriately.

The translations and rotations of the master input device 204 (and its reference frame 456) are mapped (also "transformed") to the instrument 404's reference frame to provide a control relationship between the master input device 204 and the instrument 404 by using well-known kinematic calculations.

For example, where the master input device 204 is controlling the end effector 406, the translations and rotations of the master input device 204 are mapped to the end effector 406 using the reference frames 456 and 450 and kinematic calculations relating the reference frames 456 and 450; as the master input device 204's position or orientation is changed, moving the position or orientation of the reference frame 456, the end effector 406's position or orientation is changed correspondingly (moving the position or orientation of the reference frame 450), so that end effector 406's movement is controlled by to the master input device 204's movement.

As noted earlier, any number of reference frame definitions can be used for control, as long as the reference frame definitions are internally consistent and sufficient for the control system envisioned. In an implementation, the operator's frame of reference defined in Cartesian coordinates and denoted with the subscript "$_P$", $-Z_P$ is defined as motion towards the operator, and $+Z_P$ is defined as motion away from the operator. In some instances, the Z-axis may be defined according to the line of sight 408 of the field of view 427 presented to the operator in the display system 202, with $+Z_P$ defined as into the display system 202. This line of sight and associated field of view is determined by configurations such as the pose of the imaging system 402 (which can be the image capture system 108 of FIG. 1 or the imaging system mounted on a camera arm as shown in FIGS. 3A-C), any image manipulation or selection (e.g. presenting only a subset of the image) performed by the system, and the like. In this example, $-X_P$ is defined as motion toward the operator's left, and $+X_P$ is defined as motion toward the operator's right. And, $+Y_P$ is defined as motion up relative to the operator, and $-Y_P$ is defined as motion down. These Cartesian axes may be defined differently in other embodiments. For example, one or more of the pairs $+X_P/-X_P$, $+Y_P/-Y_P$, and $+Z_P/-Z_P$ may be defined oppositely. As another example, the axes may be rotated from what is shown in FIGS. 4A-B as discussed herein.

Figure 5:
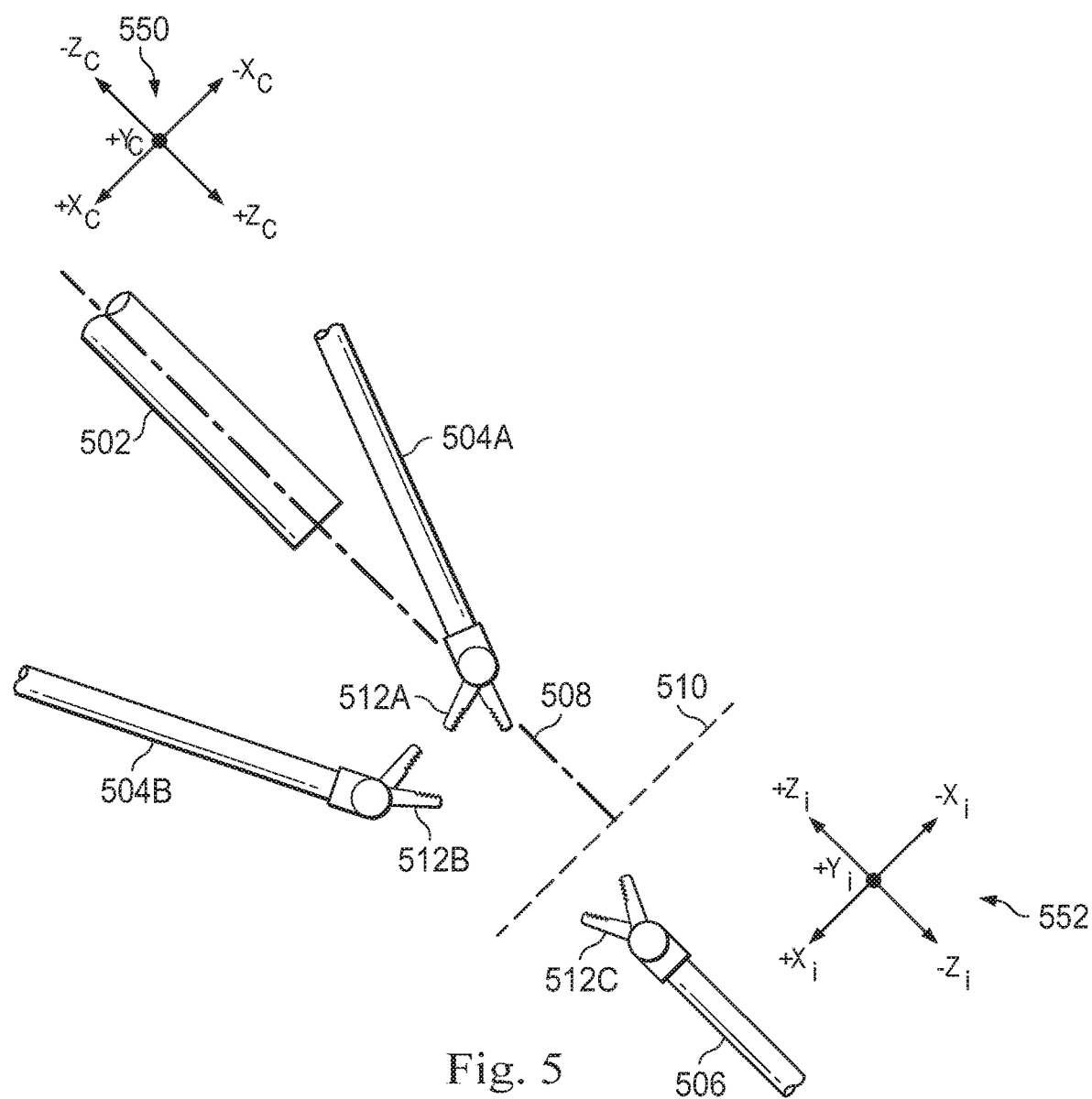
FIG. 5 depicts an arrangement of an imaging system, two primary platform instruments and a secondary platform instrument, according to some other aspects of the present disclosure.

FIG. 5 shows an arrangement of an endoscopic camera comprising the imaging system 502, two primary platform instruments 504A and 504B (collectively "primary platform instruments 504") controlled by the primary platform, and a secondary platform instrument 506 controlled by the secondary platform, all positioned around a work site (also called "operational site"). It should be understood that, although much of the following discussion is with a secondary platform instrument 506 attached to a secondary platform physically distinct from the primary platform, the same techniques and methods can also be applied to a secondary instrument attached to the primary platform. Further, the primary and secondary platforms may be physically integrated with each other, or physically separated from and moveable relative to each other.

The imaging system 502 may comprise an imaging system instrument configured to be supported by a manipulator. FIG. 5 of the present disclosure show only two primary platform instruments 504 and a single secondary instrument 506. It should be understood that embodiments of the present disclosure may include more or fewer primary instruments and more or fewer secondary instruments. In FIG. 5, a frame of reference 550 for the primary platform is shown. In the frame of reference 550 for the primary platform, $+Z_C$ is defined as the same direction as the insertion of the camera's field of view (the camera comprising the imaging system 502) (toward the bottom-right of FIG. 5). $-Z_C$ is defined as the same direction as the withdrawal of the field of view of this camera (toward the top-left of FIG. 5). Motion toward the right in the field of view of the camera is defined as $+X_C$ (toward the bottom left of FIG. 5), and motion toward the left in the field of view of the camera is defined as $-X_C$ (toward the top right of FIG. 5). Motion "up" in the field of view of the camera is defined as $+Y_C$ (out of the page in FIG. 5), and motion "down" in the field of view of the camera is defined as $-Y_C$ (into the page in FIG. 5).

In this example, the line of sight of the view provided to the operator by the display system 202 (e.g. the line of sight 408 of FIG. 4B) comes from the imaging system 502 having a line of sight 508. By mapping the movement of instruments 504 in the frame of reference for the primary platform to the movement of the input device 204 in the operator's frame of reference, the movement of instruments 504 is more intuitively related by the operator with the frame of reference shown in FIG. 4A. Generally, where the full image captured by the imaging system 502 is produced on the display system 202 without distortion or transformation (e.g. rotation, stretching, cropping, etc.), it is reasonable to model the mapping between the imaging system 502 and the view provided to the operator through the display system 202 as identity. Where distortion or transformation does occur, the mapping between the field of view of the imaging system 502 and the view provided to the operator through the display system 202 may be other than identity, and the difference can be accounted for by proper mapping. For example, the difference can be accounted for when mapping the movement of instruments 504 in the frame of reference 552 for the primary platform to movement of the input device 204 in the operator's frame of reference. Thus, the operator can translationally and rotationally move the input devices 204 to command corresponding translational and rotational movements of the instruments 504 in a more intuitive manner and more naturally relate them through hand-eye coordination.

FIG. 5 also shows a plane 510 that is orthogonal to the line of sight 508. The plane 510 is disposed between the imaging system 502 and the secondary platform instrument 506. Envisioning this plane 510 in cases where the configuration of the system allows can be helpful in understanding relative insertion positions and directions, such as by examining how manipulator arms and their associated instruments approach the plane 510. As shown, the tips of the instruments 504, the tip of the instrument 506, and the tip of the imaging system 502 are positioned such that the tips of the instruments 504 and the imaging system 502 are positioned on a same side of the plane 510. Meanwhile, the tip of the instrument 506 is on an opposite side of the plane 510. Thus, in the example, the instruments 504 are on one side of the plane 510, while the instrument 506 is on the opposite side of the plane 510.

Figure 6:
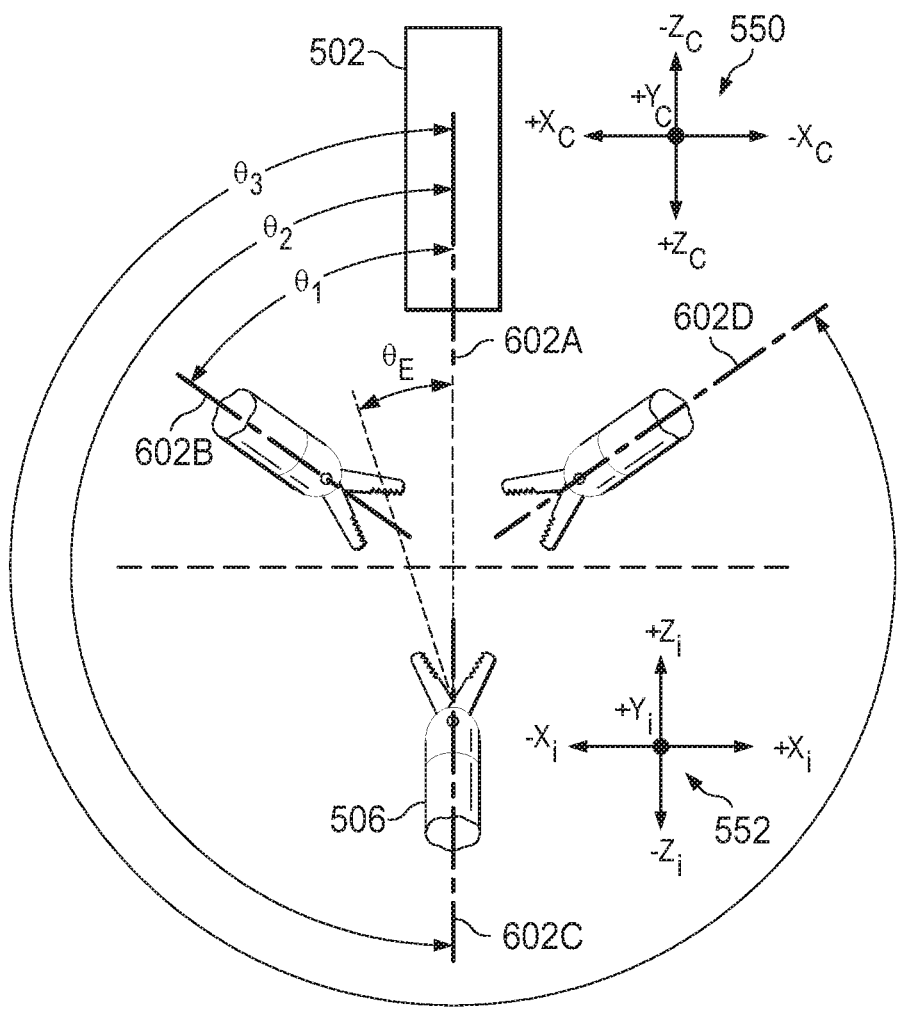
FIG. 6 depicts a perspective view of the distal portion of an imaging system instrument, the distal end of a secondary platform instrument, and the distal ends of two primary platform instruments, and a reference frame for the secondary platform instrument is shown, according to some other aspects of the present disclosure.

Referring to FIG. 6, a simplified view of the work space including the distal end of the imaging system 502, the distal end of the secondary platform instrument 506, and the distal ends of the two primary platform instruments 504 are shown. FIG. 6 also shows a reference frame 552 for the secondary platform instrument. And, for ease of explanation, FIG. 6 also shows the plane 510. Relative to the reference frame 552 for the secondary platform instrument, insertion of the secondary platform instrument toward the surgical site (and toward the plane 510) is defined as $+Z_I$, and withdrawal of the secondary platform instrument away from the surgical site and the plane 510 is defined as $-Z_I$. Motion of the secondary platform instrument to the left relative to the field of view of the imaging system 502 (toward the right in FIG. 5) is defined as $+X_I$ (the "right") for the reference frame 552, and motion of the secondary platform instrument to the right relative to the field of view of the imaging system 502 (toward the left in FIG. 5) is defined as $-X_I$ (the "left") for the reference frame 552. And, motion of the secondary platform instrument upwards relative to the field of view of the imaging system 502 (out of the page) is defined as $+Y_I$ ("up") for the reference frame 552, and motion of the secondary platform instrument downwards relative to the field of view of the imaging system 502 (into the page) is defined as $-Y_I$ ("down") for the reference frame 552. The control system 110 may determine orientations of the instruments 504 and 506 (and/or their supporting arms) with respect to the work site using any of these reference frames, including the reference frames 550, 552, or another reference frame. As shown, longitudinal axes 602A, 602B, 602C, and 602D, are associated with the imaging system 502, the primary platform instrument 504B, the secondary platform instrument 506, and the primary platform instrument 504A, respectively. As shown in FIG. 6 and in other figures, the longitudinal axes 602 may be within the $X_I$-$Z_I$ plane, the $X_C$-$Z_C$ plane, or some other plane parallel to these ordinal planes of the instrument reference frame. In other embodiments, the longitudinal axes 602 may not lie within, or be parallel to, the $X_I$-$Z_I$ plane or the $X_C$-$Z_C$ plane. Thus the axes 602, and the instruments associated with the axes 602, may or may not be coplanar, may or may not be in parallel planes, and may or may not be parallel.

As described herein, the control system 110 may determine orientational differences between the instruments present in the work site. For example, the control system may calculate an angular orientation difference $\theta_1$ between the axis 506A of the imaging system 502 and the axis 602B of the primary support instrument 504B, an angular orientation difference $\theta_2$ between the axis 602A and the axis 602C, and an angular orientation difference $\theta_3$ between the axis 602A and the axis 602D. As shown, the orientation difference $\theta_1$ is about 45°, the orientation difference $\theta_2$ is about 180°, and the $\theta_3$ is about 315°. Before the control system implements movement commands received from one of the input devices 204 of FIG. 2 to move one of the instruments, the control system 110 may determine the orientation difference associated with the instrument. The control system 110 may then determine the appropriate commands to implement, based on the orientation difference. In some embodiments, the orientation difference $\theta_X$ between the two axes may be determined as the arccosine of the dot product of the axes (e.g. as the inner product of two vectors, each vector representing a direction along one of the two axes). Other methods may also be utilized.

Referring again to FIG. 5, it can be seen that motion of one of the primary platform instruments 504 is performed in the primary platform's reference frame. The motion of a master input device 204 in the operator's (physician's or other user's) reference frame shown in FIG. 4A is mapped to the motion of that primary platform instrument 504 in the platform's reference frame (defined by the field of view of the imaging system 502 and what part of the field of view). Thus, when a master input device 204 is moved to the right, the system causes a coupled primary platform instrument, either of 504A and 504B in this example, to move to the right relative to the primary platform's reference frame 550. To provide intuitive control to the user for the secondary platform instrument 506 as it appears in the primary platform's reference frame 550, motion of a master input device 204 may be mapped to motion of the secondary platform instrument 506 in the secondary platform's reference frame 552 in a reversed (inverted) manner. This reversal (inversion) may be implemented in a variety of ways. For example, the mapping may include reversing (inverting) motion in at least one axis of the reference frame 552. As another example, a rotation may be applied in determining instrument 506 motion such that the instrument 506 motion is reversed. As a further example, at least one axis of the reference frame 552 may be reversed when the instrument 506 is inserted oppositely to the imaging system 502.

Since the secondary instrument 506 may be pointed generally toward the imaging system 502 and its field of view, if the master input device 204B controls the secondary platform instrument 506, then a "withdraw" motion on the master input device 204B in a −Z direction relative to the operator frame of reference, in accordance with aspects of this invention, correspond to a "withdraw" motion of the secondary platform instrument 506 in the platform reference frame 550 and an "insert" motion of the secondary platform instrument 506 in the instrument frame of reference 552. In other words, in some aspects of this invention, a withdraw motion on the master input device 204B, which moves the input device 204B toward the operator, is mapped by the system to motion of the secondary platform instrument 506 toward the imaging system 502, and toward the operator's eyes if viewing the display system 202 of FIG. 2 (assuming the display system 202 is showing the image obtained by the imaging system 502). Similarly, a motion to the right on the master input device 204B (relative to the operator) corresponds to a motion to the left of the secondary platform instrument 506 (relative to the instrument 506), so that the distal end of the secondary platform instrument 506 appears to move to the right in the imaging system 502's field of view. Likewise, a motion to the left on the master input device 204B (relative to the operator), in accordance with aspects of this invention, correspond to a motion to the right of the secondary platform instrument 506 (relative to the instrument 506), so that the distal end of the secondary platform instrument 506 appears to move to the left in the imaging system 502's field of view. In these aspects of the invention, motion up and down of the master input device 204B still corresponds to motion up and down of the secondary platform instrument 506 as seen by the operator in the display system 202.

For the user, the perception when viewing the image of the work site is as if the distal tip of the secondary platform instrument 506 is grasped and moved by the input device 204B, and the shaft of the secondary instrument 506 follows along. This perception is in contrast to the user's perception when moving a primary platform instrument 504A or 504B, in which the user envisions that the hands of the user grasping the input device 204 are the end effectors of the primary platform instrument 504A or 504B.

In some embodiments, the shaft of the secondary instrument 506 may comprise one or more compliant portions, or may have one or more joints, such that a distal end of the shaft may move differently from a proximal portion of the shaft. For example, in some implementations, a distal end of the shaft of the secondary platform instrument 506 moves in the desired direction while the proximal end of the shaft of the secondary platform instrument 506 stays stationary, moves parallel to the desired direction to a different amount, move in a direction opposite direction to the desired direction, etc. In other embodiments, the distal and proximal ends of the second platform instrument 506 may move in the same direction.

The following table, Table 1, shows exemplary correspondence in the various reference frames. This table assumes that the reference frames are attached to their respective components, and are not redefined relative to their respective components during operation.

TABLE 1

| Master input device motion in user's reference frame | Primary platform instrument motion in camera reference frame (primary platform reference frame) | Secondary platform instrument motion in camera reference frame (primary platform reference frame) | Secondary platform instrument motion in secondary platform instrument reference frame |
|---|---|---|---|
| $+X_P$ | $+X_C$ | $+X_C$ | $-X_I$ |
| $-X_P$ | $-X_C$ | $-X_C$ | $+X_I$ |
| $+Y_P$ | $+Y_C$ | $+Y_C$ | $+Y_I$ |
| $-Y_P$ | $-Y_C$ | $-Y_C$ | $-Y_I$ |
| $+Z_P$ | $+Z_C$ | $+Z_C$ | $-Z_I$ |
| $-Z_P$ | $-Z_C$ | $-Z_C$ | $+Z_I$ |

It can be seen that the positive and negative directions in the secondary reference frame are defined to correspond to the desired directions of motion in the camera instrument reference frame (and thus with respect to the operator's perspective as facilitated by the display system 202 in various implementations). Optionally, insertion-withdrawal and left-right directions in the secondary platform instrument reference frame can be defined to be the same as the directions of the camera instrument reference frame, in which case the signs would be reversed in Table 1 for the insertion-withdrawal and left-right directions in the secondary platform reference frame.

Before implementing a movement command received by one of the input devices 204 to control the secondary platform instrument 506, the orientation relative to the imaging system 502 is determined by the control system 110. This may be done by referring to stored data, such as an entry in a table associated with the secondary platform instrument 506. For example, some instruments may be identified when coupled to a slave manipulator arm as a type of instrument typically utilized in an oppositional configuration. Accordingly, because of the identity or type of the instrument, the control system 110 may determine that a transform (also referred to as "mapping") comprising one or more inversions (for example, like that shown in Table 1 or another transform relationship) or other adjustments is to be made to properly relate the reference frame of that instrument to the reference frame of the imaging system 502.

In some implementations, the transforms may be implemented as one or more matrices comprising vectors or scalars. These transforms are applied by the control system 110 when determining instrument motion based on input device motion information received from the input devices 204. Depending on the implementation, a series of matrices and other calculations may be applied to invert (or otherwise rotate), translate, or scale and generate control signals for controlling the motion of the instruments. Any appropriate transformation mechanism may be used. For example, a rotational transform may be implemented by a rotation matrix (or series of rotation matrices) representing a difference between the orientations of two reference frames.

The orientation differences between instruments may be determined through any appropriate manner. For example, some implementations use image processing, orientation sensors, kinematic information, shape sensing information, some other technique, or a combination of techniques to determine the orientations or orientation differences between instruments. In all cases, comparison with an orientation difference threshold may be used to select an appropriate transform. For example, as shown in FIG. 6, the orientation difference between the imaging system 502 and the secondary platform instrument 506 is about 180°; in this example, the control system 110 applies a transform to invert the mapping of the motion of the secondary platform instrument 506 relative to the input device 204 along at least one axis. In some implementations, orientation differences below 180° may also be assigned the same transform to invert the mapping of the motion of the secondary platform instrument 506 relative to the input device 204 along at least one axis. In some implementations. For example, orientation differences in a range of about 135° to about 225° may be assigned the same transform as shown in Table 1. In another embodiment, orientation differences in a range of about 120° to about 255° may be assigned a transform shown in table 1. In some implementations, the orientation difference may be defined as an absolute orientation difference such that an orientation difference of 240° is processed the same as an orientation difference of 1200, or an orientation difference of 90° is processed the same as an orientation difference of 270°.

Additionally, some embodiments of the control system 110 may apply different transforms depending on the orientation difference. For example, while the transform shown in Table 1 may be applied to any instruments having an orientation difference relative to the imaging system ranging from about 120° to about 180°, a second transform may be applied to any instruments having an orientation difference relative to the imaging system ranging from about 90° to about 120°, and a third transform may be applied to any instruments having an orientation difference relative to the imaging system ranging from about 270° to about 300°.

For example, the second transform may associate the +Z direction of a reference frame defined by the imaging system with the +X direction of a reference frame of the secondary platform instrument. The third transform may associate the +Z direction of the imaging system frame with the −X direction of the reference frame of the secondary platform instrument. In some embodiments, the second and third transforms may only be applied to certain types of instruments, and not applied to other types of instruments.

As described herein, the control system 110 may adjust an orientation mapping between input device and instrument, when the instrument has an orientation difference relative to the field of view of the work site that exceeds an adjustment threshold. In some implementations, the control system does not further adjust the orientation mapping. In some implementations, the control system 110 may also adjust the mapping to include an ergonomic offset to facilitate movement by the operator. An exemplary offset is shown in FIG. 6 as $\theta_E$ between the axis 602C of the secondary platform instrument 506 and an axis 604, representing the axis of the shaft of the input device 204 that is to control the secondary platform instrument 506. The ergonomic offset may provide for a certain degree of difference between the orientation of the input device 204 assigned to control a particular secondary platform instrument, like the secondary platform instrument 506, and the orientation of that secondary platform instrument. This may be helpful where a mapping without an ergonomic offset is awkward. For example, some implementations use an ergonomic offset that emulates the input device holding the shaft of the instrument 506 like a pencil, and enable a pencil-like interaction with the secondary platform instrument 506. As such, the interactions between the input device 204 and the secondary platform instrument 506 resemble the off-axis interaction between pencil and paper when writing, for example.

Accordingly, with such an ergonomic offset, the operator may move the input device 204B, for example, to cause movement of the second platform instrument 506 without bringing the shaft 206B into perfect axial alignment with the secondary platform instrument 506. An angular ergonomic offset ranging from about 0° to about 50° may be utilized by the control system 110, based on factors such as user selectable adjustments, user preferences, the type of instrument comprising the secondary platform instrument 506, etc. In some implementations, this angular ergonomic offset may be implemented as a rotation matrix added to a series of matrices linking the reference frame of the input device 204B and the instrument 506. In some implementations, this is implemented as a rotation of the secondary platform instrument frame 552.

Embodiments of the present disclosure may include a primary instrument platform and a secondary instrument platform that are connected to separate and movable bases that rests on the floor of the operating room or work environment during operation. Embodiments may additionally include primary and secondary instrument platforms that are separate and movable with respect to each other but that are attached to a common structure such as a rail extending alongside a table T. Additional embodiments may also include primary and secondary instruments that are secured to a common base or platform, but that approach an work site of opposite sides of a plane orthogonal to a line of sight provided by an endoscopic instrument, such that controlling the secondary instruments in a natural-feeling way requires adjusting or applying a transform to received input commands.

Figure 7A:
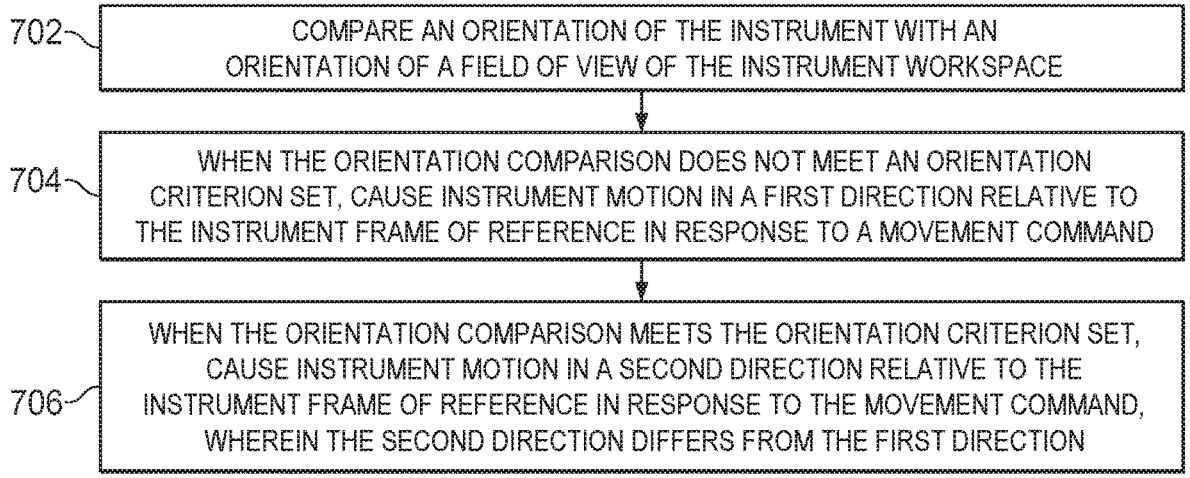
FIG. 7A is a diagram showing a flowchart of a method for generating control signals for the secondary platform instrument, according to some other aspects of the present disclosure.

Embodiments of the present disclosure provide for many different modes of operation. One of these mode of operation is depicted in the flowchart of FIG. 7A, which illustrates a method 700A of controlling a robotic system including primary and secondary platforms. Several methods are illustrated in the accompanying figures and described herein. Embodiments of the illustrated methods may include additional operations before, after, in between, or as part of the enumerated operations. Additionally, some embodiments of the illustrated methods may omit one or more of the enumerated operations. Moreover, some embodiments of the illustrated methods may include combinations of operations from the depicted methods. Some embodiments of the methods include computer readable, non-transient, tangible media having instructions thereon that when executed by a processor, such as the processing device of the control system 110 cause the control system to perform corresponding operations in the context of the described medical systems.

Some embodiments of the method 700A may begin at an operation 702 in which a processing device of a robotic control system compares an orientation of an instrument with an orientation of a field of view of the instrument workspace. For example, the control system 110 may compare the orientation of the secondary platform instrument 506 relative to the orientation of the imaging system 502, which provides a field of view of the workspace to an operator. In some embodiments, the orientations may be compared by comparing the axis 602A with the axis 602C. In some embodiments, the orientation difference is determined in view of planes associated with the imaging system 502 and the secondary platform instrument 506, such that only certain components of the axes are compared. As shown, the orientation difference is approximately 180°.

At operation 704, when the orientation comparison does not meet an orientation criterion set, the control system causes instrument motion in a first direction relative to the instrument frame of reference in response to a movement command. For example, when the orientation difference is less than an orientation threshold, such as 125°, 115°, or 95°, a movement command to move the instrument in an insertion direction may be implemented by the control system 110 by moving the instrument in the insertion direction defined relative to the imaging system 502. The orientation difference may be a total orientation difference in 3D space, or it may be an orientation difference when the insertion and viewing directions are projected onto a single plane. For example, the orientation difference may be when the directions are projected onto the X-Y plane, the X-Z plane, or the Y-Z plane defined by the imaging system reference frame or the instrument reference frame.

In some embodiments, the operator may select a desired orientation threshold prior to operating the system 100. Other orientation difference thresholds may be utilized in other embodiments. In some embodiments, the orientation difference threshold may be defined by a cone or pyramid extending away from the imaging system 502 and centered on a line of sight thereof. Accordingly, the orientation difference threshold may be independent of the role of the imaging system 502 in some embodiments. The orientation criterion set may also include factors associated with particular types of instruments. Accordingly, a secondary platform instrument having an ablation end effector may have a different threshold compared to a secondary platform instrument having forceps as its end effector. Additionally, the orientation criterion set may include information to distinguish which instruments are associated with which platform. For example, in some embodiments the orientation criterion set may include an indication that the instrument 506 is a secondary platform instrument, in that the instrument 506 is coupled to a system that is characterized by the control system 110 as a second platform. Combinations of these criteria may be used in comparing an instrument to a criterion set.

At operation 706, when the orientation comparison meets the orientation criterion set, the control system causes the instrument motion in a second direction relative to the instrument frame of reference in response to the same movement command. The second direction differs from the first direction. For example, the second direction may be opposite the first direction. Other examples of different directions are shown in Table 1.

In this way, the control system 110 may adjust or apply a movement command mapping (also called "transform") when the orientation difference indicates that the secondary platform instrument is positioned opposite an intermediary plane, like the plane 510 shown in FIGS. 5 and 6, such that it is more natural from the operator's perspective to move the secondary platform instrument in a direction different than would be dictated by the reference frame of the secondary platform instrument.

Figure 7B:
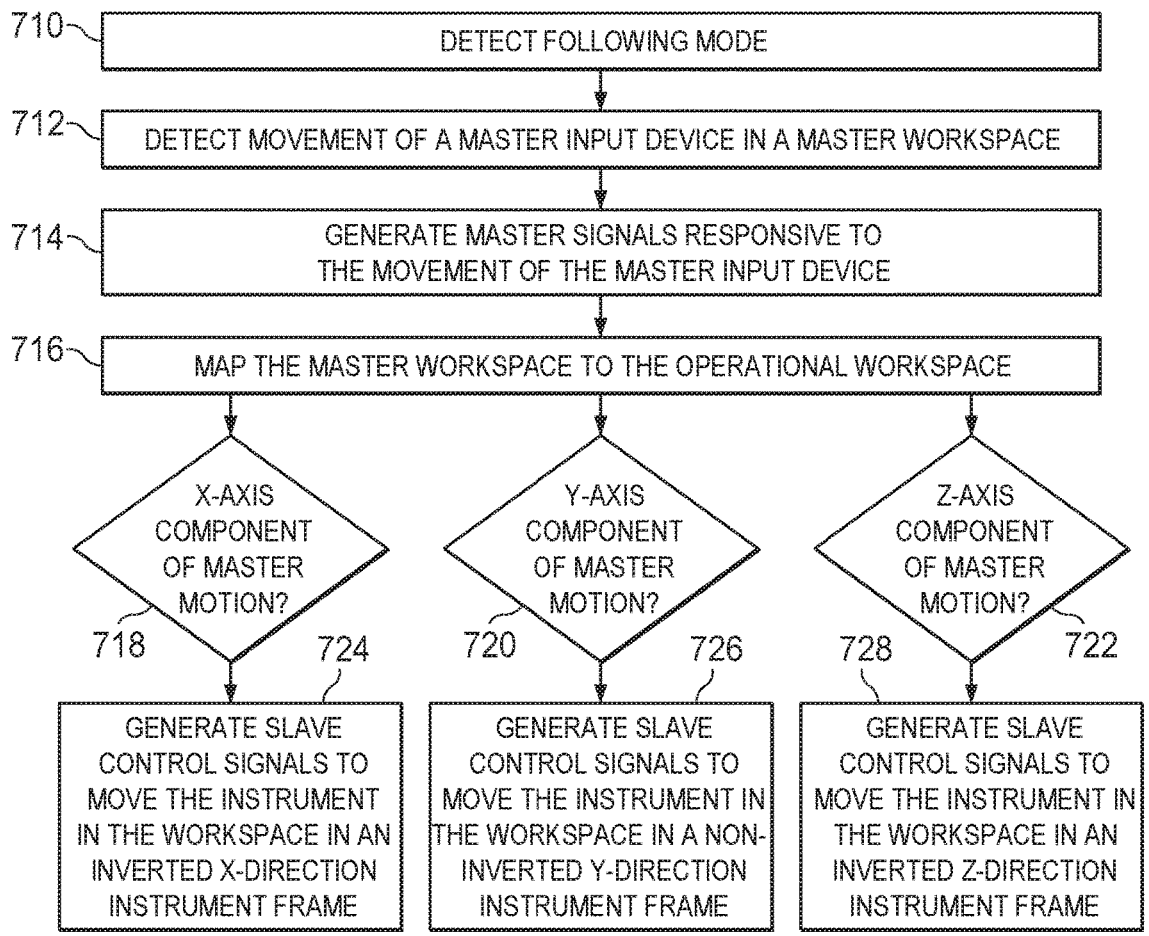
FIG. 7B is a diagram showing flowchart of another method for generating control signals for the secondary platform instrument, according to some other aspects of the present disclosure.

Another exemplary embodiment is shown as a flowchart of a method 700B in FIG. 7B. The method 700B describes one of many different modes of operation of the system 100, showing a "following mode" of operation, in which a slave instrument follows the motion of a master manipulator. For example, the secondary platform instrument 506 may "follow" the motion of the input device 204B. The secondary platform instrument may also be referred to as an external instrument (EI), because it is external to the primary platform in at least some embodiments. FIG. 7B is a diagram that shows a general flow for generating control signals for the secondary platform instrument (EI).

And the illustrated embodiment of the method 700B may begin at operation 710 in which the control system or processing device of the control system to detect that the system is operating in the following mode. At operation 712, the control system detects movement of a master input device in a master workspace. For example, the control system 110 may detect movement of the input device 204B within the area in which the input device 204B can move.

At operation 714, the control system generates master signals that are responsive to the movement of the master input device. For example, the control system 110 may generate master signals that correspond to the movement of the input device 204B. These master signals may be, comprise, or cause movement commands. At operation 716, the control system maps the motion in the master workspace to motion in a surgical workspace or other work site. For example, the control system 110 may map or translate the movement commands received from the input device 204B to an instrument reference frame associated with the instrument, such as the instrument 506 that is to be moved based on the movement commands. As described herein, when the orientation of the instrument to be controlled differs substantially from the field of view provided by the imaging system 502, the transform or transforms may be applied to the movement commands in order to map them to the work site so that they can be appropriately implemented by the instrument 506. Implementing movement of the instrument 506 may be the same as implementing movement of a manipulator arm supporting the instrument 506.

In order to map the master workspace to the work site, the method 700B may include checks of individual components of the commanded motion. As shown in FIG. 7B, an X-axis component check is performed at operation 718, a Y-axis component is checked at operation 720, and a Z-axis component is checked at 722. The operations 718, 720, and 722 may be performed serially or in parallel by the control system 110. Because commanded motion generally includes components along more than one of the X-axis, Y-axis, and X-axis, the operations 718, 720, and 722 may be performed for any and all commanded motions associated with instruments that can be identified by any criteria, such as the orientation criterion set.

At operations 724, 726, and 728, the transformed control signals may be produced by the control system. As shown, at operation 724, based on the check performed at operation 718, the control system generates slave control signals to move the external instrument or secondary platform instrument 506 in an inverted X-axis direction in the frame of reference of the secondary platform instrument 506. Similarly, at operations 726 and 728, the control system 110 may generate a slave control signals to move the secondary platform instrument in an inverted Y-axis or Z-axis, respectfully, in the frame of reference of the secondary platform instrument 506. In some embodiments of operations 724, and/or 726, and/or 728, one or more of the generated control signals may include non-inverted control signals. As shown, the checks at operations 720 and 726 may result in the generation of non-inverted signals for the Y-axis (at operation 726) and in the generation of inverted signals for the Z-axis (at operation 728.) The checks performed at operations 718, 720, and 722 may rely on a set of criteria, including orientation criteria, to determine whether an inversion modification should be made. The checks perform at operations 718, 720, and 722 may indicate that one or more of the control signal components are not to be inverted or otherwise modified. In such instances, one of more of the operations 724, 726, and 728 may not be performed, such that one or more of the X-axis, and/or Y-axis, and/or Z-axis will not be inverted by the control system. In some embodiments, an applied transform may modify a movement by an angle that is less than 180°, i.e., that only partially inverts a movement command.

Figure 8A:
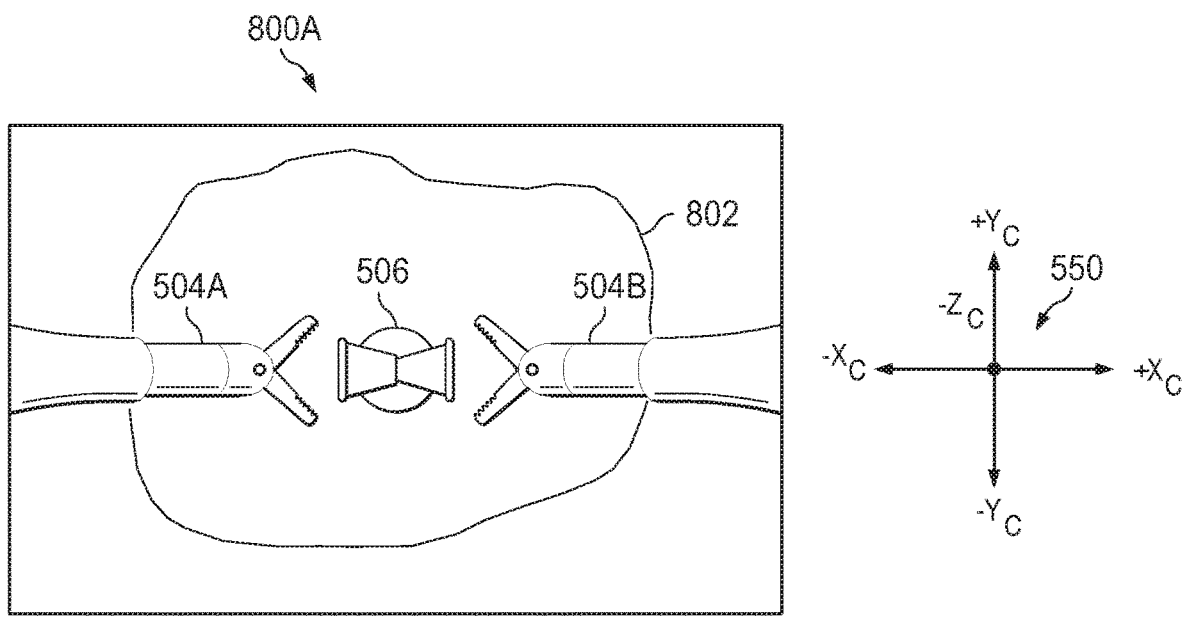
FIG. 8A is diagrammatic view of from of an displayed image for an operator, in which two primary platform instruments are shown, and the distal tip of the secondary platform instrument is shown, according to some other aspects of the present disclosure.

FIG. 8A is diagrammatic view 800A of as seen from an operator's perspective via the display system 202, displaying video from the imaging system 502. FIG. 8A shows two primary platform instruments 504A and 504B, and the distal tip of the secondary platform instrument 506. This perspective is representative of the primary platform camera instrument's perspective, because the user's eye reference frame is mapped to the primary platform camera instrument's reference frame.

Figure 8B:
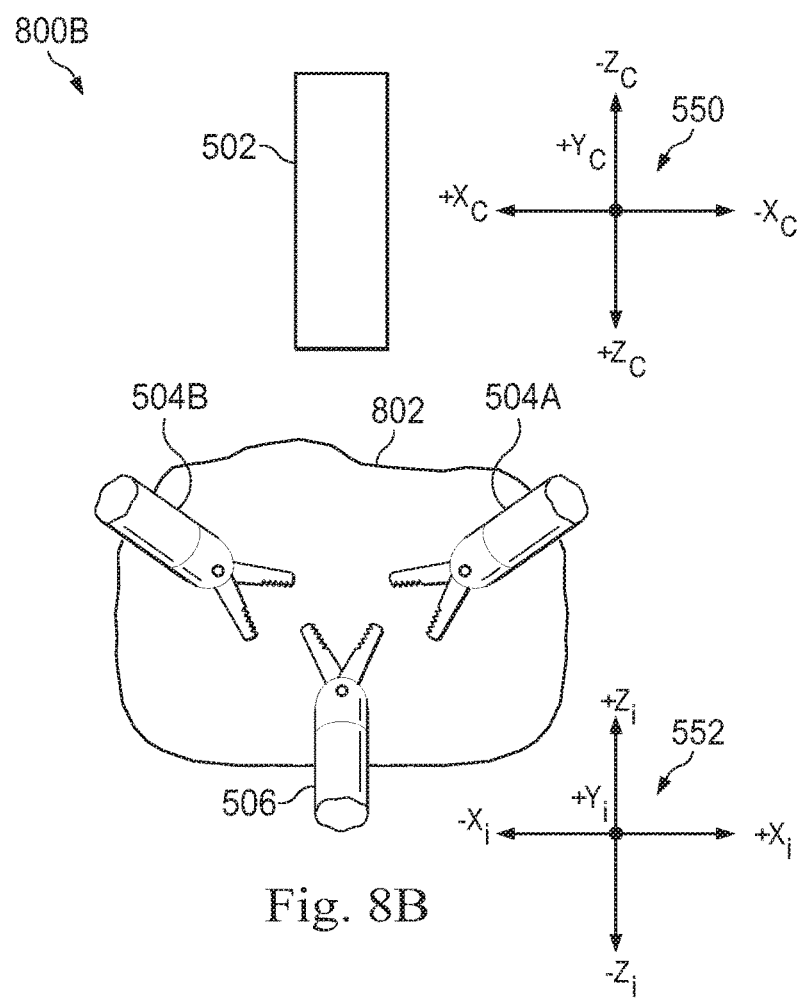
FIG. 8B is a diagrammatic view of the distal ends of two primary platform instruments and the distal end of a secondary platform instrument, according to some other aspects of the present disclosure.

FIG. 8B is a diagrammatic view 800B of the distal ends of the primary platform instruments 504 and the distal end of the secondary platform instrument 506. This view is provided for purposes of explanation, as the instruments, in some embodiments, are positioned at or near a work site 802 within the body of the patient P. FIG. 8B also shows an exemplary camera reference frame near the depiction of the imaging system 502, and an exemplary instrument frame near the instrument 506. This exemplary instrument frame is associated with the secondary platform instrument 506.

Figure 9A:
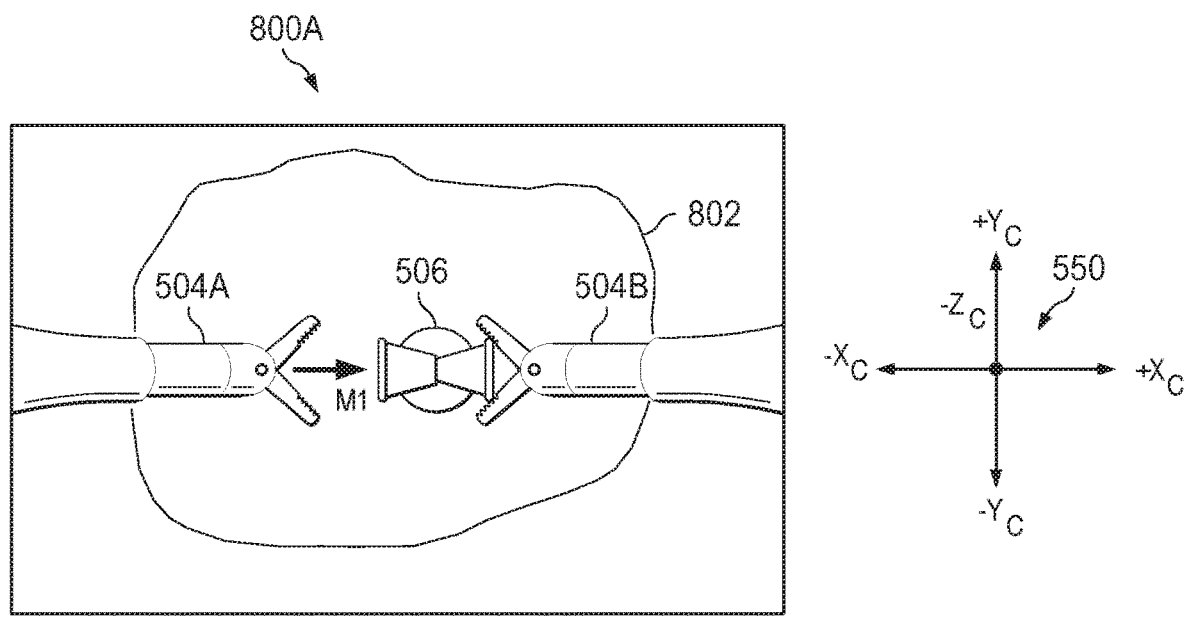
FIGS. 9A and 9B are corresponding views showing movement of the secondary platform instrument, in both the camera reference frame and the secondary platform reference frame, according to some other aspects of the present disclosure.
Figure 9B:
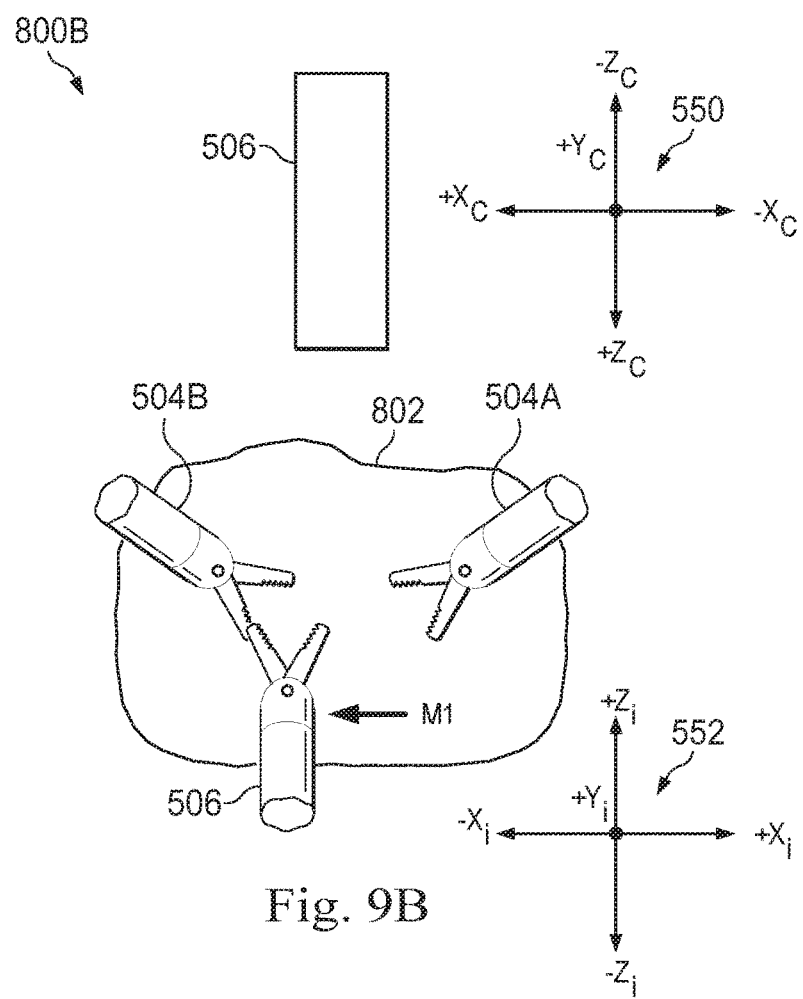

FIGS. 9A and 9B are perspective views that show movement M1 of the distal end of the secondary platform instrument 506 along the X-axis in the left-right direction, in both the camera reference frame (which may be considered to be the same as the operator's reference frame, in some embodiments) and the secondary platform reference frame. It should be noted that in some implementations, the display system 202 may not be directly in front of the operator as shown in FIG. 2. For example, the operator may be viewing a display system off to the right side of the operator, such that the operator's head is turned to the right relative to the operator's torso, arms, and hands. The operator's proprioception may enable the operator to move an input device 204 to the right of the operator, to cause an instrument to move to the right in the image shown on the display system. However, in other embodiments, other frames of reference may be used. For example, the operator's movement may be detected and/or processed in relation to the display system (thus using a display system-based frame of reference instead of a operator-body-based frame of reference).

As shown in FIGS. 9A and 9B, motion M1 to the right in the user/camera reference frame (FIG. 9A) corresponds to movement M1 to the left in the secondary platform reference frame (FIG. 9B). The control system 110 may effect the movement M1 by receiving a command from the operator, while the operator sees the view 800A in the display system 202 of FIG. 2. When the operator is controlling the secondary platform instrument 506 and the operator desires to move the distal end of the instrument 506 to the operator's right, the operator moves the hand-held manipulator (for example, input device 204B, although the input device 204A may also be used). The control system 110 modifies the movement commands, adjusting or applying a transform so that appropriate movement commands can be implemented in the instrument reference frame. To implement the movement commands in a way that produces the operator's desired result, the transform (or "mapping") applied by the control system 110 causes the movement M1 to be implemented by moving the instrument 506 in the –X direction in the reference frame of the secondary instrument 506.

Figure 10A:
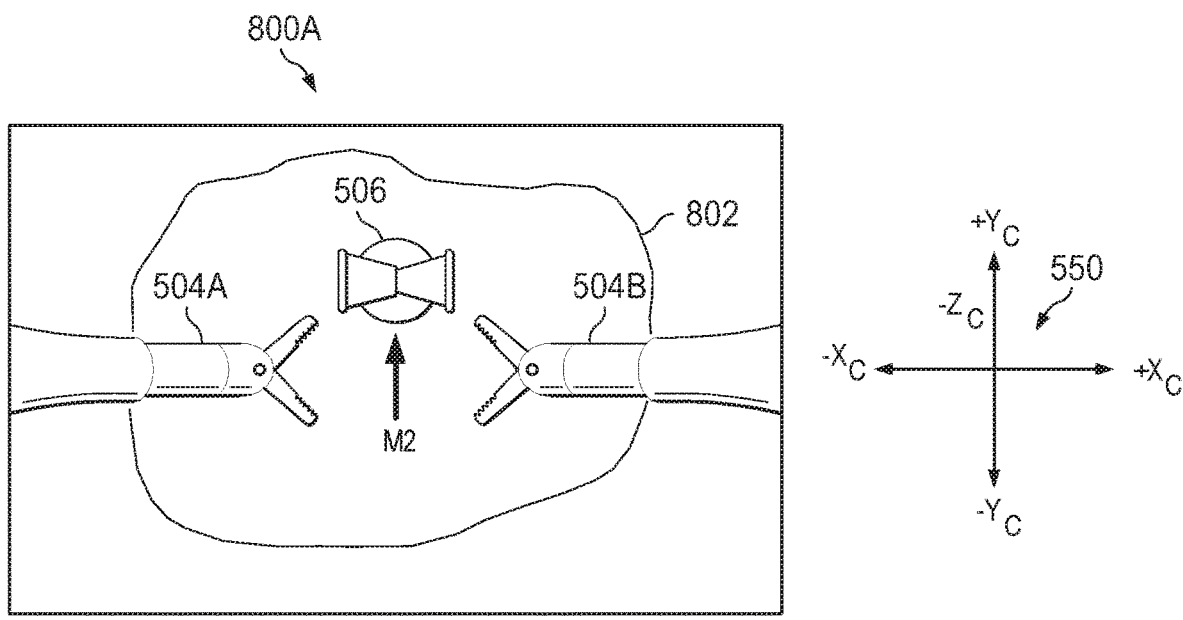
FIGS. 10A and 10B are corresponding views showing movement of the secondary platform instrument, in both the camera reference frame and the secondary platform reference frame, according to some other aspects of the present disclosure.
Figure 10B:
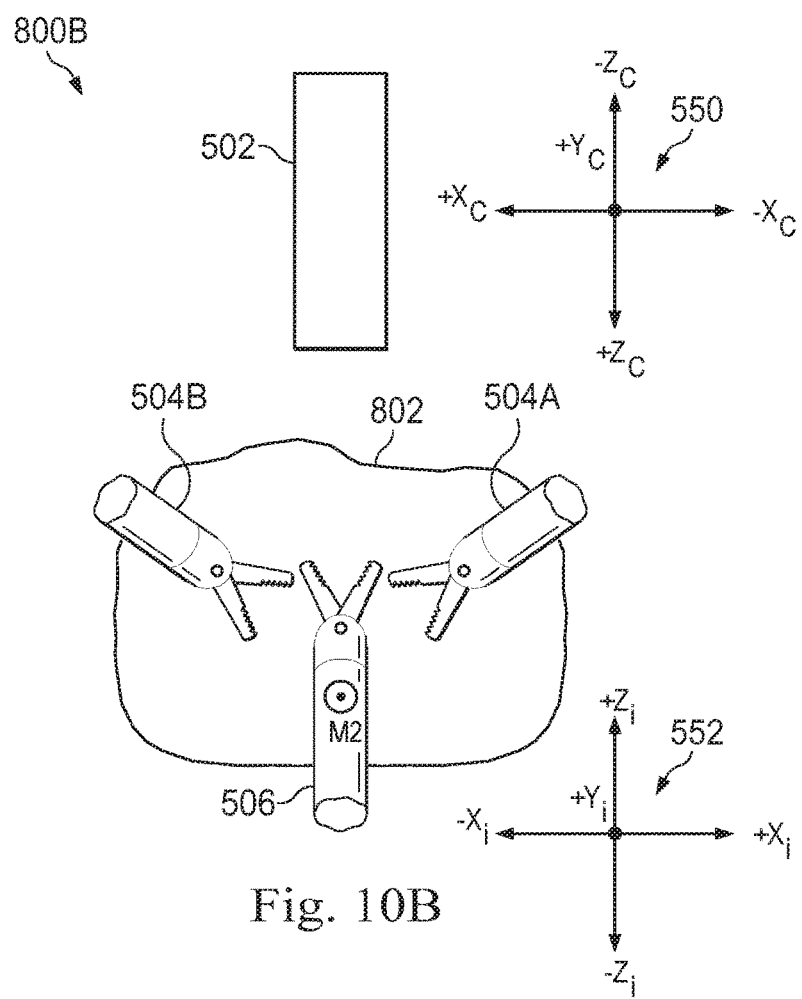

FIGS. 10A and 10B are perspective views that show movement M2 of the distal end of the secondary platform instrument 506 along the Y-axis or in the up-down direction, in both the camera reference frame and the secondary platform instrument reference frame. Motion M2 up in the camera reference frame (FIG. 10A) corresponds to movement up in the secondary platform reference frame (FIG. 10B). The control system 110 may effect the movement M2 by receiving a command from the operator, while the operator sees the view 800A in the display system 202 of FIG. 2. When the operator is controlling the secondary platform instrument 506 and the operator desires to move the distal end of the instrument 506 toward the top of the operator's view, the operator moves the hand-held manipulator (for example, input device 204B, although the input device 204A may also be used). The control system 110 may modify the movement commands, adjusting or applying a transform so that appropriate movement commands can be implemented in the instrument reference frame. To implement the movement commands in a way that produces the operator's desired result, the transform (or "mapping") applied by the control system 110 causes the movement M2 to be implemented by moving the instrument 506 in the +Y direction in the reference frame of the secondary instrument 506. In some embodiments, the control system 110 may determine that no transform needs to be applied to the Y directional component of the movement M2. However, if the movement M2 is not exclusively in the plane of the Y-axis, the control system 110 may apply or adjust a transform to the component of the movement M2 that is not in the Y-axis plane.

Figure 11A:
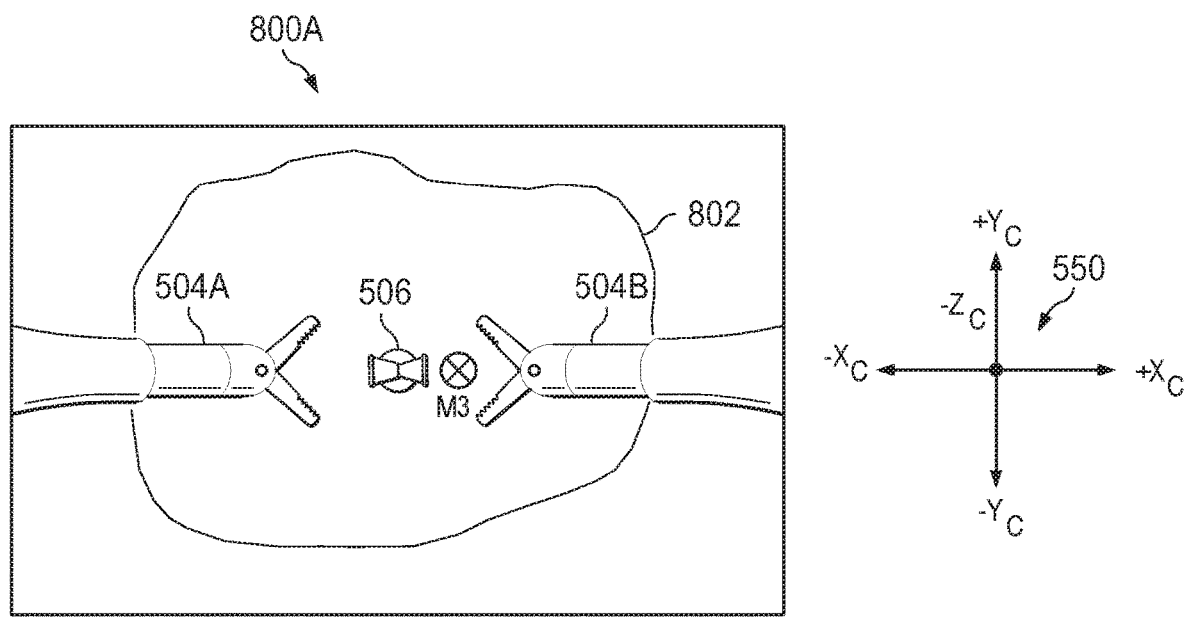
FIGS. 11A and 11B are corresponding views showing movement of the secondary platform instrument, in both the camera reference frame and the secondary platform reference frame, according to some other aspects of the present disclosure.
Figure 11B:
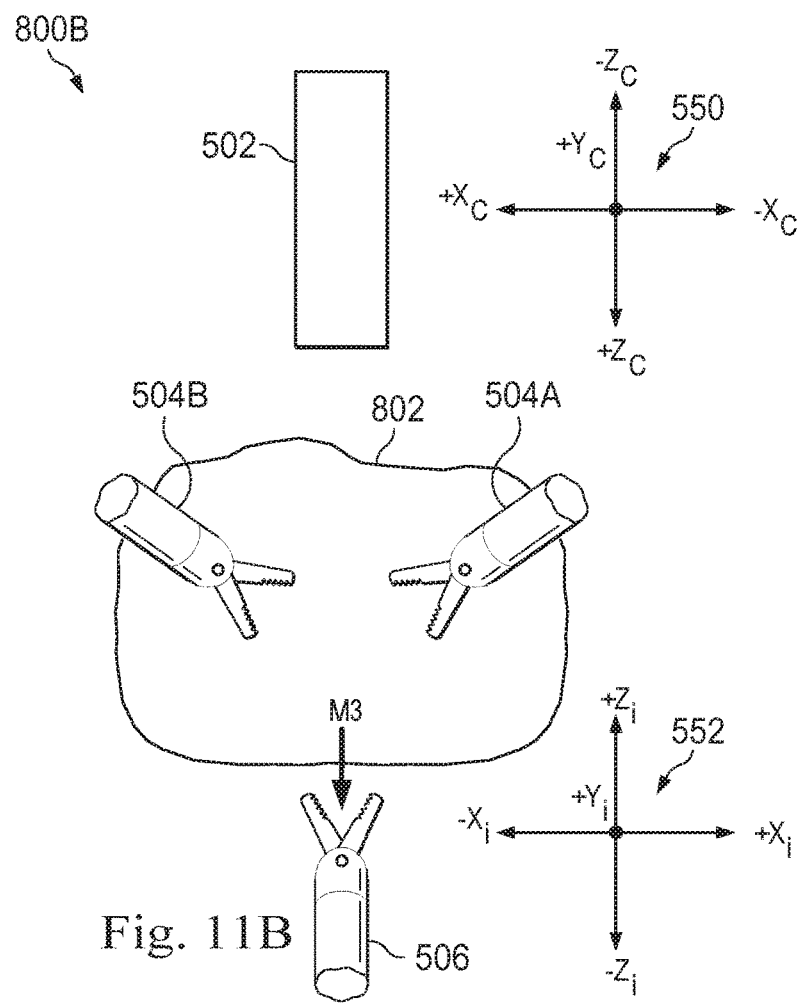

FIGS. 11A and 11B are perspective views that show movement M3 of the secondary platform instrument 506 along the Z-axis or in the insertion-withdrawal direction, in both the camera reference frame and the secondary platform reference frame. Insertion motion in the camera reference frame (FIG. 11A) corresponds to withdrawal motion the secondary platform reference frame (FIG. 11B). The control system 110 may effect the movement M3 by receiving a command from the operator, while the operator sees the view 800A in the display system 202 of FIG. 2. When the operator is controlling the secondary platform instrument 506 and the operator desires to move the distal end of the instrument 506 to away from the operator's view, the operator moves the hand-held manipulator (for example, input device 204B, although the input device 204A may also be used) away from the operator's torso, or in the +Z direction in the operator's reference frame, which corresponds to the camera reference frame. The control system 110 modifies the movement commands, adjusting or applying a transform so that appropriate movement commands can be implemented in the instrument reference frame. To implement the movement commands in a way that produces the operator's desired result, the transform (or "mapping") applied by the control system 110 causes the movement M3 to be implemented by moving the instrument 506 in the –Z direction in the reference frame of the secondary instrument 506.

Various forms of the following modes of FIGS. 7A and 7B, and shown in other figures, are optionally used in various primary platforms. For example, in an "adjust mode" motion of the master input device 204A or 204B moves the imaging system 502 so that the distal end of a camera instrument comprising the imaging system 502 correspondingly moves in the camera reference frame and relative to the tissue at the work site 802. In the adjust or adjustment mode motions of the primary instruments are coupled to the camera motion so that the distal ends of the primary platform instruments 504A and 504B are anchored in the camera reference frame and do not move relative to the tissue at the work site. While the distal ends are anchored in the camera reference frame and do not move relative to the tissue at the work site, the proximal ends of the primary platform instruments 504A and 504B may move in order to compensate or adjust for the movement of the proximal end of the camera instrument comprising the imaging system 502. In the adjust mode, the motion of the secondary platform instrument is optionally also coupled to the camera motion so that the distal end of the secondary platform instrument is anchored in the camera reference frame and does not move relative to the tissue at the work site. Anchoring the instruments in space relative to the tissue assists safety, since the instrument distal ends do not move relative to the tissue and so may be grasping tissue or will not be inadvertently moved into contact with tissue. The adjust mode may be used for small changes of camera position or orientation.

Figure 12:
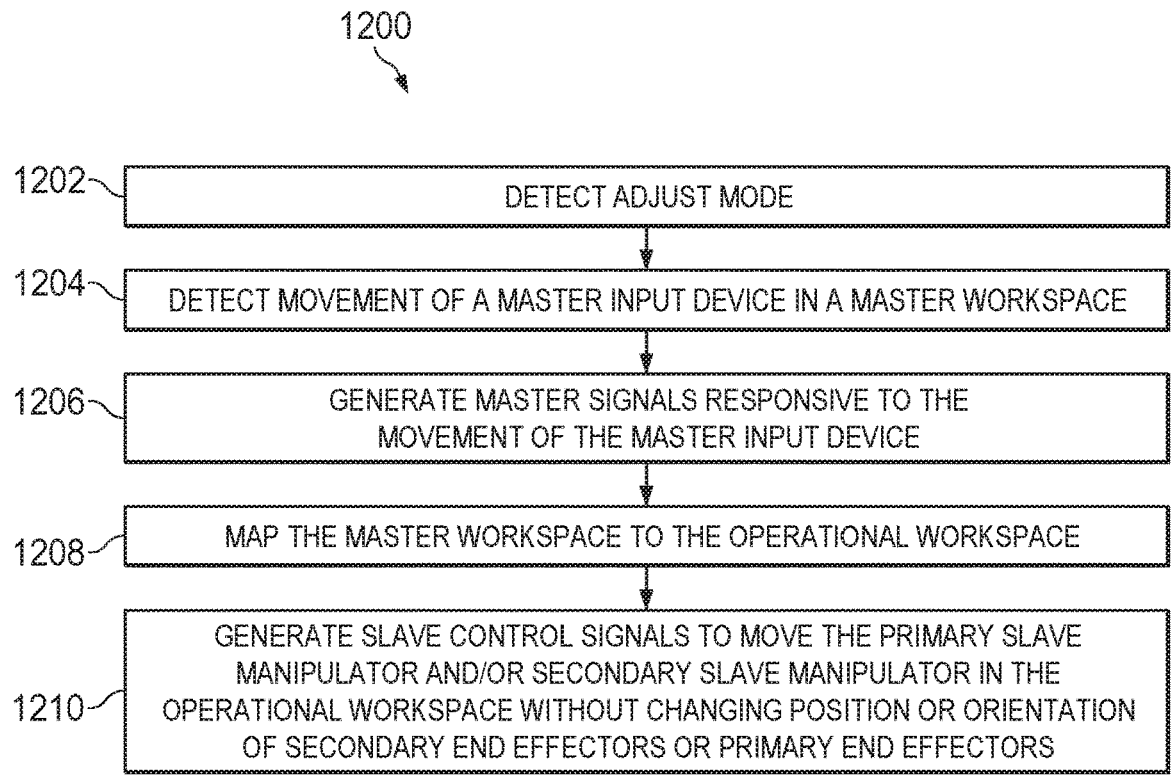
FIG. 12 is a flowchart showing a method of general operation of the secondary platform instrument in an adjust mode, according to some other aspects of the present disclosure.

FIG. 12 is a flow diagram that shows a general operation of the secondary platform instrument in the adjust mode. The method 1200 shown in FIG. 12 may begin at operation 1202 in which the control system detects that movement commands are to be implemented according to an adjust mode. When the control system 110 detects that the input device 204 is moving or has moved (operation 1204), the control system may generate master control signals responsive to that movement. These master control signals may be expressed in a frame of reference associated with the input device 204. At operation 1208, the control system may map the master workspace to the surgical or other workspace. For example, the control system 110 may generate or identify a transform that can be applied to the master control signals, which are expressed in the frame of reference of the manipulator, so that they can be appropriately applied to a selected slave manipulator, like the instrument 506 or the arm that supports and positions the instrument 506.

At operation 1210, the control system may generate slave control signals to move the primary slave manipulator and/or the secondary or external slave manipulator in the surgical or other workspace without changing the position orientation of the end effectors of the slave manipulators. For example, the control system 110 may move the proximal ends of the instruments 504A, 504B, and/or 506 in a way that minimizes or eliminates motion at the distal end of these instruments so that the end effectors 512 maintain their position and orientation within the work site. This may be done to permit the imaging system 502 to be repositioned or to facilitate a desired range of motion of one or more of the instruments present in the work site.

Figure 13:
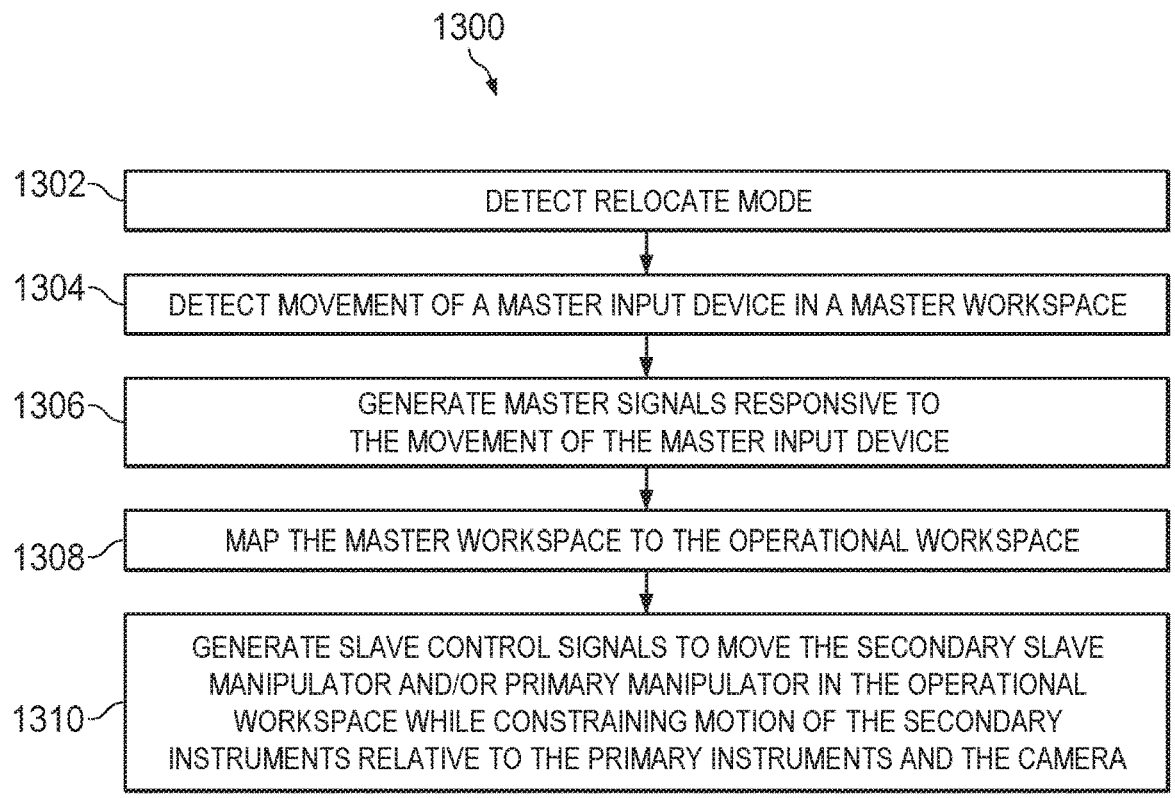
FIG. 13 is a flowchart that shows a method of general operation of the secondary platform instrument in the reposition mode, according to some other aspects of the present disclosure.

Referring now to FIG. 13, shown therein is another exemplary mode of operation as a method 1300 for a "relocate mode" motion of the master manipulator. During operation of the system 100, the operator may move the primary platform camera instrument in a mode in which the distal end of the camera instrument correspondingly moves in the camera reference frame and relative to the tissue at the work site. In the relocate mode, motions of the other primary instruments may be coupled to the primary platform camera motion so that the distal ends of the primary platform instruments move together with the camera instrument in the camera reference frame. Thus, the camera instrument and the primary platform instrument distal ends all move together relative to tissue at the surgical or other work site. In the relocate mode, the motion of the secondary platform instrument may optionally be coupled to the camera motion so that the distal end of the secondary platform instrument moves in the camera reference frame and moves relative to the tissue at the work site. Similarly, the control system 110 applies appropriate transforms to secondary platform instruments so that the secondary platform instruments are also moved relative to the surgical or other work site in a way that maintains the secondary platform instrument end effectors in a fixed relationship to the primary platform camera motion. The relocate mode may be used for large changes of camera position or orientation. FIG. 13 is a flow diagram of a method 1300 for general operation of the secondary platform instrument in the relocate mode.

Embodiments of the method 1300 may begin at an operation 1302 in which the control system detects that the system is in a relocate mode. At operation 1304, the computing system may detect movement of a master input device in a master workspace. For example, the control system 110 may detect movement of one of the input devices 204 within the area defined by the constraint range of motion of the input devices 204. At operation 1306 the control system may generate master signals responsive to and corresponding to the movement of the master input device. At operation 1308, the control system may map the master workspace to the surgical or other workspace. As described herein, mapping input device motion in the master workspace to instrument motion in the work workspace may include applying or adjusting a transform to the master control signals to translate them from the master workspace, such as the operator's reference frame or camera reference frame, to the instrument reference frame. In doing so, the control system may, at operation 1310 generate corresponding slave control signals to move a slave manipulator or manipulators in the surgical or other workspace while constraining motion of the secondary or external platform instrument relative to the imaging system and/or the primary instruments. In this way, when the operator moves the imaging system 502, secondary platform instrument 506 may be moved within the workspace so that it remains stationary relative to the imaging system 502. The transform (or "mapping") applied to the master control signals is different for the secondary platform instrument 506 than for the primary platform instruments.

In operating modes in which motion of the secondary platform instrument 506 is coupled to motion of the primary platform camera, motion constraints of the secondary platform instrument 506 (e.g., physical joint limits, position along the Z-axis relative to a cannula through which the secondary platform instrument is inserted that may constrain motion of the instrument, and the like) optionally may be used to establish motion limits of the primary platform camera. Such camera instrument motion limits optionally may be absolute, or optionally a user may override a motion limit such as by moving a master manipulator past a virtual, haptic wall (a virtual barrier implemented by force feedback impeding movement past the barrier).

Figure 14:
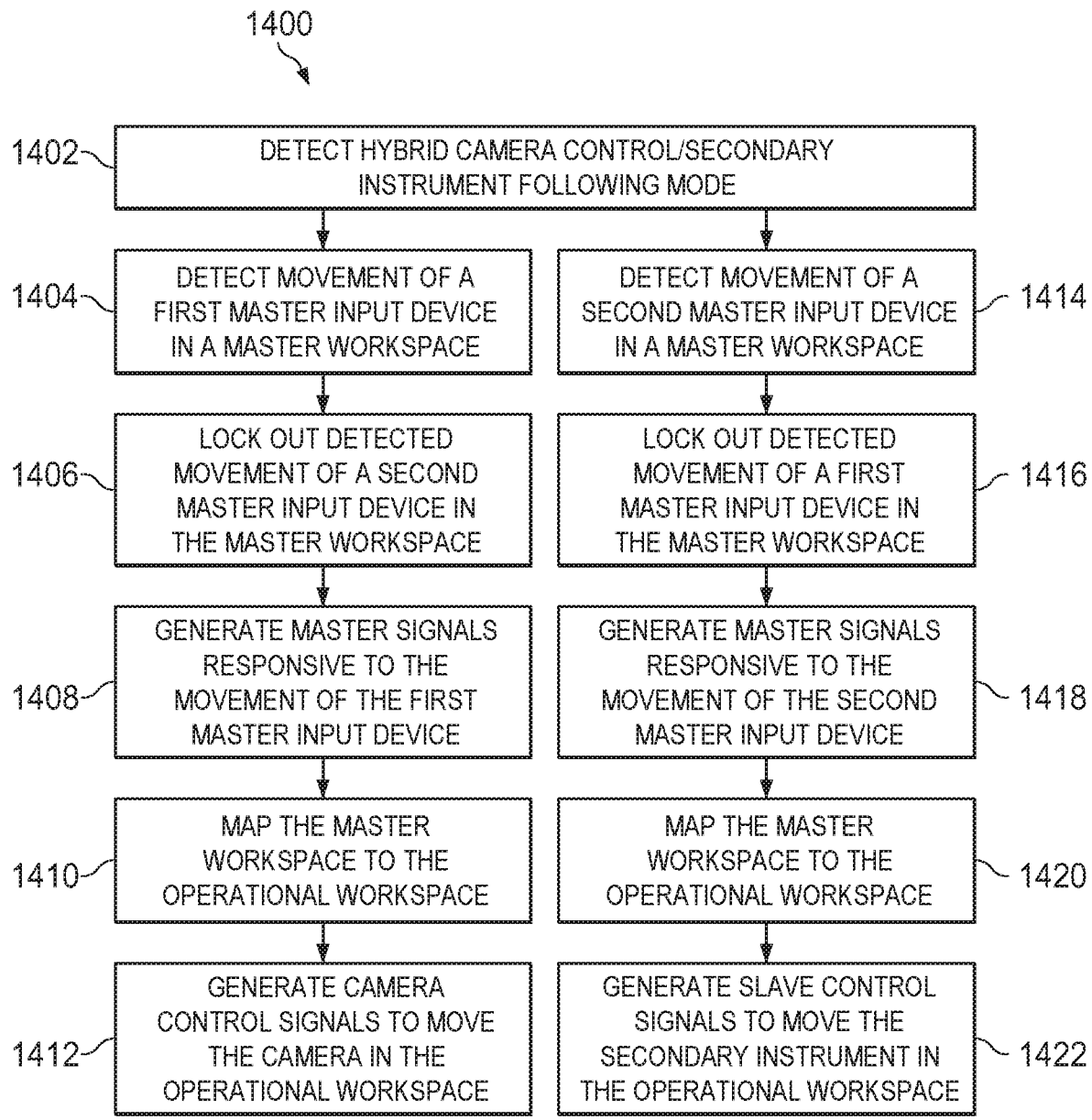
FIG. 14 is a flowchart that shows a method of general operation in a hybrid camera control and secondary platform instrument control mode, according to some other aspects of the present disclosure.

FIG. 14 is a flow diagram that shows a method 1400 for a hybrid camera control and secondary platform instrument control mode. In an example hybrid mode, a first master manipulator controls motion of the primary platform camera instrument, and a second master controls motion of the secondary platform instrument. Motion of one of the camera instrument or the secondary platform instrument is prohibited if motion of the other is occurring. In such an operating mode, the control system 110 ensures that the correct mapping of master input device motions in the operator (user) reference frame and imaging system (camera) reference frames occurs for either the camera instrument or the secondary platform instrument.

At operation 1402, the control system determines that the hybrid control mode is in effect. The determination of the control mode may be obtained by querying state information of the control system 110. At operation 1404, the control system 110 may detect movement of a first master input device in a master workspace such as the input device 204A. Upon detection of the movement of the input device 204A, the control system may lock out a detected movement of a second master input device, such as the input device 204B, at operation 1406. At operation 1408, the control system may generate master signals responsive to the movement of the first master input device and then map the master workspace to the surgical or other workspace in order to implement the movement commands included in the master signals, at operation 1410. At operation 1412, the control system may generate camera control signals to move the camera in the surgical or other workspace. For example, the control system 110 may move the imaging system 502 according to the reference frame of the imaging system 502. At operation 1414, the control system may detect movement of the second master input device in the master workspace. For example, the control system 110 may detect movement of the input device 204B. In order to prevent any unwanted interaction between the instrument being controlled by the input device 204B and the instrument being controlled by the input device 204A, the control system 110 may lock out any subsequently detected movement of the first master input device, e.g. the input device 204A, at operation 1416. At operation 1418, the control system may generate master signals responsive to the movement of the second master input device. The control system may map the master workspace to the surgical or other workspace at operation 1420 in order to appropriately generate slave control signals to move the secondary platform instrument in the surgical or other workspace at operation 1422.

Figure 15:
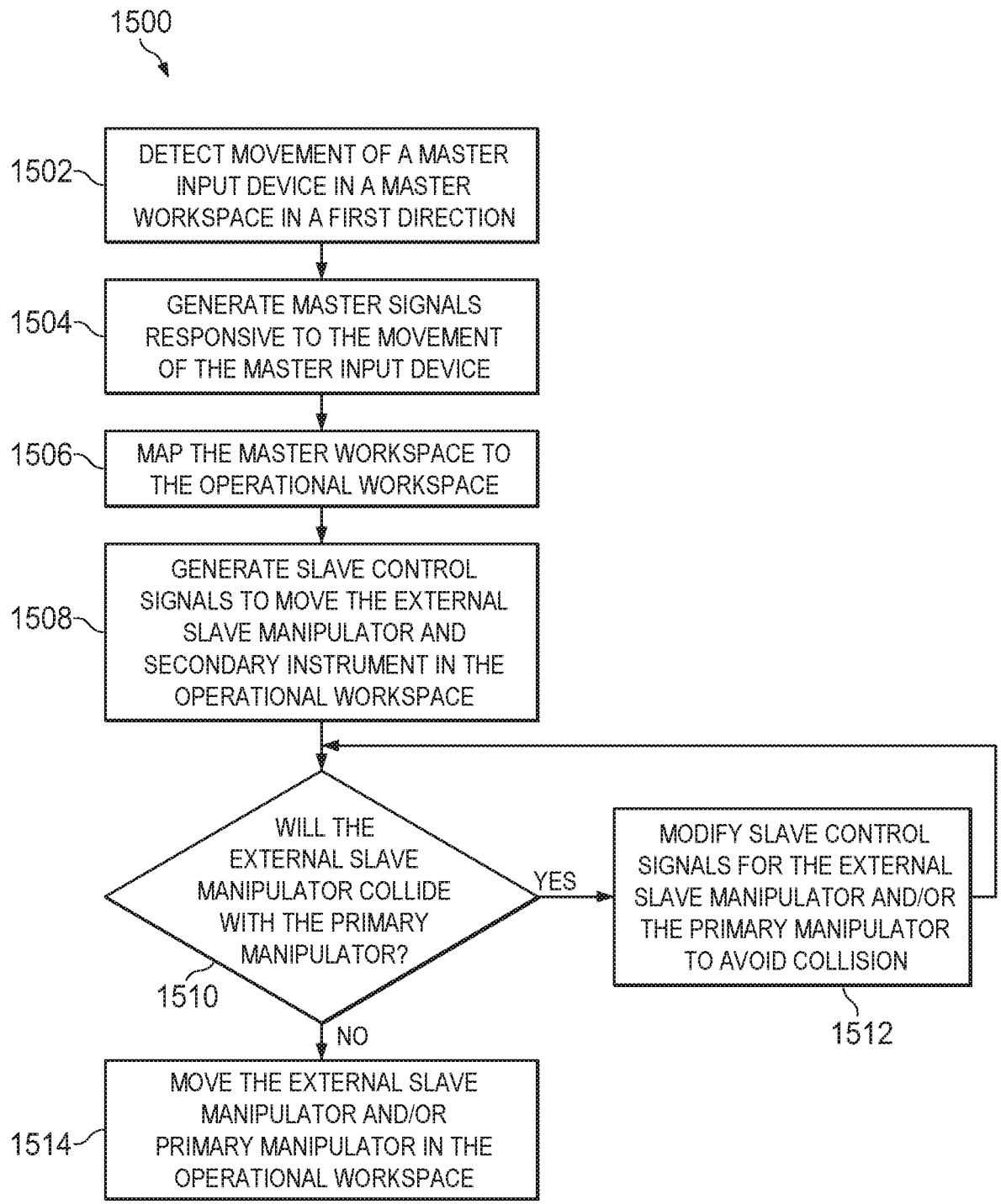
FIG. 15 is a flowchart that shows a method of general operation of a collision avoidance aspect of motion of the secondary platform instrument, according to some other aspects of the present disclosure.

FIG. 15 is a flow diagram of a method 1500 for a collision avoidance aspect of motion of the secondary platform instrument. If the control system 110 determines that movement of the secondary platform instrument 506 will result in a collision with a primary platform instrument, either 504A or 504B, the control system may optionally modify the control of one or both of the secondary and primary platform instruments so that the predicted collision will not occur as the secondary instrument moves. For example, when controlling the secondary platform instrument, the user may feel haptic sensation in the master manipulator to "steer around" a potential collision with a primary platform instrument. As another example, the user may observe a primary platform instrument move slightly during motion of the secondary platform instrument to visually communicate the potential collision to the operator. Collision avoidance aspects may be implemented in some or all of various operating modes, such as following, adjust, and relocate modes described above.

Some embodiments of the method 1500 may begin at operation 1502 in which the control system detects movement of a master input device in a master workspace, the movement being in a first direction. At operation 1504, the control system 110 may generate master signals responsive to the movement of the master and put device, which may be the input device 204B as shown in FIG. 5. At operation 1506, the control system 110 may map the master workspace to the surgical or other workspace, identifying relationships between the operator reference frame or camera reference frame and the instrument reference frame of the instrument being controlled by the master input device. At an operation 1508, the computing system generate control signals to move the external slave manipulator or secondary platform instrument in the work site. At operation 1510, the control system 110 uses kinematic or non-kinematic sensor information associated with each of the slave manipulator and their associated instruments to determine whether the movement will cause the secondary platform instrument to collide with one of the primary platform instruments. If so, the control system 110 modifies the slave control signals at operation 1512 either or both of the secondary platform instrument and the primary platform instrument in order to avoid the collision. In some embodiments, the control system 110 may modify the slave control signals to cause one slave manipulator to move around the other slave manipulator in order to avoid the collision. This may cause the moving slave manipulator to be moved to the desired location, but via a path that is different than the path dictated by the commanded motion received from the input device 204B. Additionally or alternatively, some embodiments of the operation 1512 may include moving the slave manipulator that is not associated with the input device 204B, in order to avoid the collision or to alert the operator to enable the operator to avoid the collision. In some implementations, the control system 110 may verify a state of the slave manipulator to avoid any additional complications. For example, if the primary slave manipulator has forceps as an end effector, the forceps being closed to grasp tissue, the control system 110 may determine that the forceps or closed and/or grasping tissue and prevent responsive movement of the primary slave manipulator that might otherwise be implementable to avoid the collision. The state information may alternatively be able to qualify the movement of the primary slave manipulator, limiting the movement thereof to a wiggle or other motion that is visible to the operator but that will not result in damage to the tissue being grasped.

Returning to the method 1500, if the external slave manipulator is determined not to be on a path resulting in collision with the primary manipulator at the determination of operation 1510, the control system may move the external slave manipulator and/or primary slave manipulator in the surgical or other workspace, at operation 1514, as directed by the movement commands produced by the operator interacting with the input devices 204.

Figure 16:
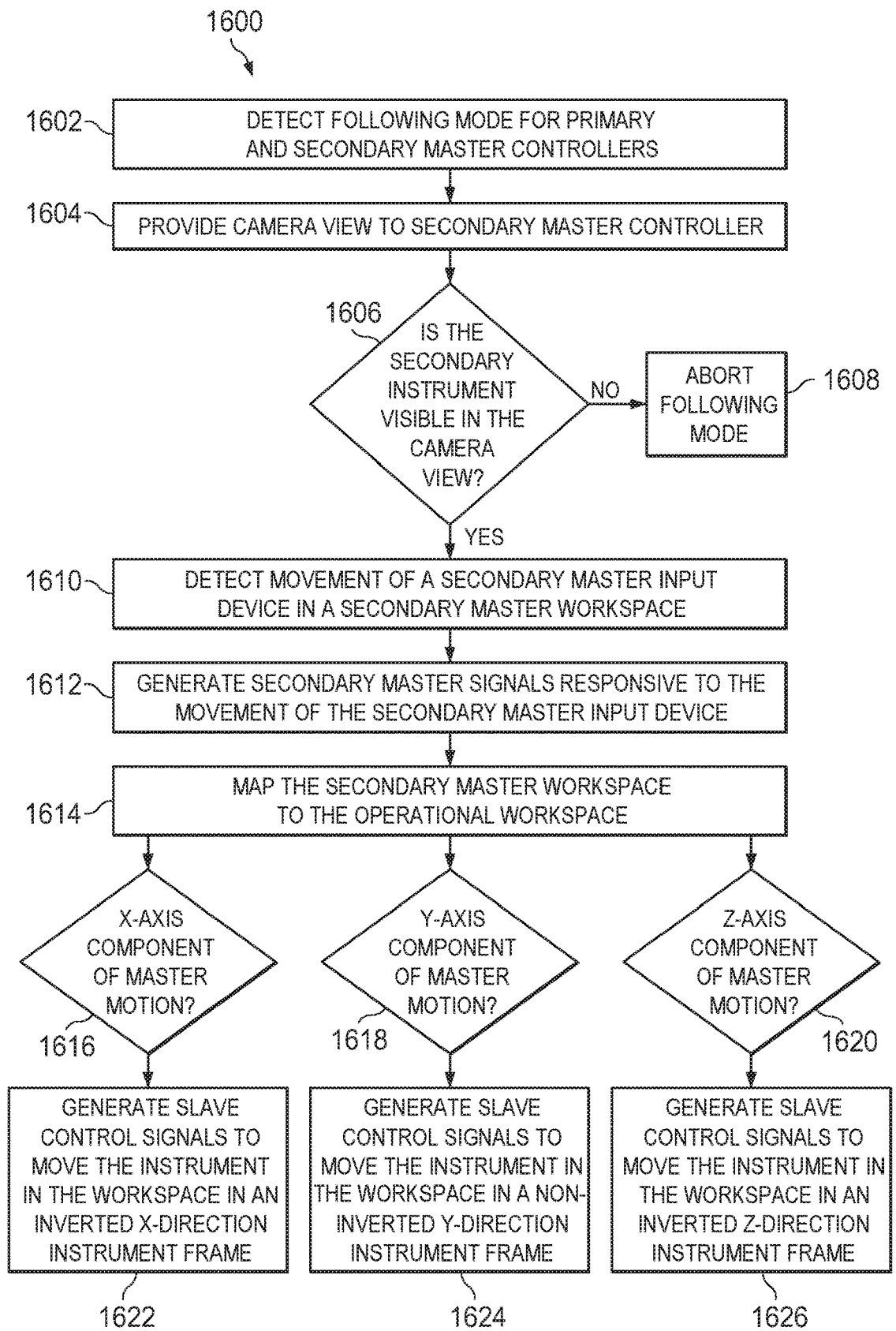
FIG. 16 is a flowchart that shows a method of controlling a secondary platform instrument by more than one operator at one than one control console, according to some other aspects of the present disclosure.

As shown in FIG. 16, aspects of the current invention may be implemented in surgical or other systems that include two or more operator's consoles, like the console 200, so that a first operator (user) viewing the work site controls a first master manipulator and a second operator (user) viewing the work site controls a second master manipulator. For example, the first operator may control the primary platform instruments, and the second operator may control the secondary platform instrument. Both the first and second operators view the same video image from the primary platform camera instrument.

FIG. 16 includes a method 1600 for controlling robotic manipulators. And the illustrated embodiment of the method 1600 may begin at operation 1602 in which the control system or processing device of the control system to detect that the system is operating in the following mode and is communicating with a primary master controller or console and a secondary master controller or console. In some implementations, the control system may verify that both of the consoles have the same state or mode in effect. At operation 1604, the control system provides the camera view to the secondary console in addition to the first console. At operation 1606, the control system 110 may use image analysis and/or kinematic information to determine whether the external instrument or secondary platform instrument is visible in the camera view. When the secondary platform instrument is not visible in the camera view, the control system may abort the following mode at operation 1608. When the secondary platform instrument is visible in the camera view, the control system may detect movement have a secondary master input device in a secondary master workspace, at operation 1610. For example, the control system 110 may detect movement of an input device 204 of the second console, like the console 200 of FIG. 2. The second console may include a master workspace defined by the limits of the motion of the input devices 204.

At operation 1612, the control system generates secondary master signals that are responsive to the movement of the secondary master input device. For example, the control system 110 may generate master signals that correspond to the movement of the input device 204B of the second console. These master signals may be movement commands. At operation 1614, the control system maps the secondary master workspace to the surgical or other workspace. For example, the control system 110 may map or translate the movement commands received from the input device 204B of the second console to an instrument reference frame associated with the instrument, such as the instrument 506 that is to be moved based on the movement commands. As described herein, when the orientation of the instrument to be controlled differs substantially from the field of view provided by the imaging system 502, the transform or transforms may be applied to the movement commands in order to map them to the work site so that they can be appropriately implemented by the instrument 506. Implementing movement of the instrument 506 may be the same as implementing movement of a manipulator arm supporting the instrument 506.

In order to map the master workspace to the work site, the method 1600 may include checks of individual components of the commanded motion. As shown in FIG. 16, an X-axis component check is performed at operation 1616, a Y-axis component is checked at operation 1618, and a Z-axis component is checked at 1620. The operations 1616, 1618, and 1620 may be performed serially or in parallel by the control system 110. Because commanded motion generally includes components along more than one of the X-axis, Y-axis, and X-axis, the operations 1616, 1618, and 1620 may be performed for any and all commanded motions associated with instruments that can be identified by any criteria, such as the orientation criterion set.

At operations 1622, 1624, and 1626, the transformed control signals may be produced by the control system. The transformed control signals may be based on the checks performed at 1616, 1618, and 1620. As shown, at operation 1622, the control system generates slave control signals to move the external instrument or secondary platform instrument 506 in an inverted X-axis direction in the frame of reference of the secondary platform instrument 506. Also as shown, the checks at operations 1618 and 1626 may result in the generation of non-inverted signals for the Y-axis (at operation 1624) and in the generation of inverted signals for the Z-axis (at operation 1626.) Similarly, at operations 1624 and 1626, the control system 110 may generate a slave control signals to move the secondary platform instrument in an inverted Y-axis or Z-axis, respectfully, in the frame of reference of the secondary platform instrument 506. The checks performed at operations 1616, 1618, and 1620 may rely on a set of criteria, including orientation criteria, to determine whether an inversion modification should be made. For example, the check performed at operation 1618 may determine that operation 1624 should not be performed, i.e. that the slave control signals moving the instrument in the Y-axis direction should not be inverted or otherwise altered. In some embodiments, an applied transform may modify a movement by an angle that is less than 180°, i.e., that only partially inverts a movement command.

In another implementation, the secondary platform may include a secondary platform camera instrument, such that two camera instruments are present in a work site. In this situation, the relation of the secondary platform to the primary platform is the same as the relation of the primary platform to the secondary platform as described above. Thus the control system 110 maps (or control systems in each of the primary and secondary platforms work together to map) the correct camera reference frame to the correct operator console, and both the first and second operators control the primary and secondary platform instruments as described above, depending on how the primary and secondary platform instruments are coupled to follow motions of the primary and secondary platform master manipulators.

In still another optional implementation, operation in a following mode or a coupled motion mode is restricted on the condition that an instrument or full instrument cluster is present in a camera field of view. Thus the second operator would be prevented from operating an instrument (e.g., operating the second master manipulator to control the secondary platform instrument) if the instrument is not visible in the video image the second operator is viewing. In another optional implementation, operation in a following or coupled motion mode is allowed if the instrument or full instrument cluster is not visible in the video image the second operator is viewing, but a warning is presented to the second operator that informs that the instrument or portion of the full instrument cluster is not visible.

Figure 17:
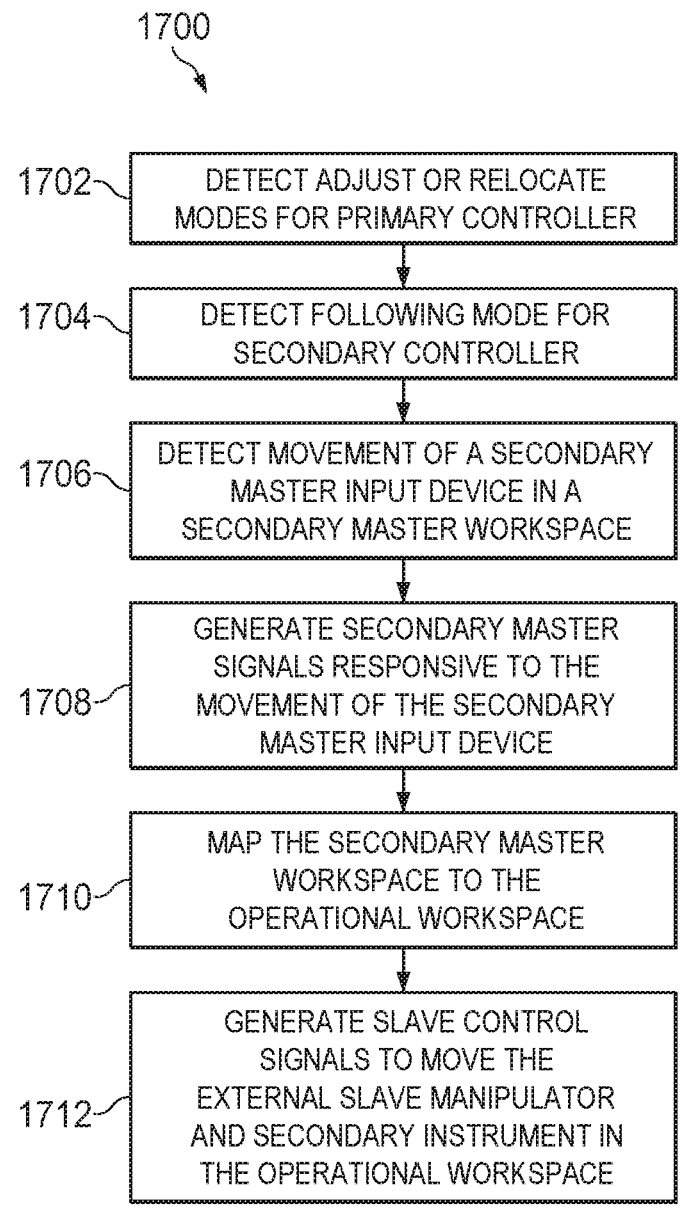
FIG. 17 is a flowchart that shows a method for adjusting and relocating modes of operation, according to some other aspects of the present disclosure.

In implementations that include a second operator console, the adjust and relocate modes of operation as described above may be implemented, as shown in the general operating flow in FIG. 17. At operation 1702, the control system detects from state information that the primary master controller or console is in an adjust mode or a relocate mode as described herein. At operation 1704, the control system detects that the secondary master controller or console is in a following mode as described herein. At operation 1706, the control system detects movement of a secondary master input device in a secondary master workspace. For example, the control system 110 may detect movement of the input device 204 of the second console. At operation 1708, the control system generates secondary master signals responsive to the movement of the secondary master input device. At an operation 1710, the control system maps the secondary master workspace to the surgical workspace, interventional site, or other work site as described herein. At the operation 1712, the control system generates slave control signals to move the external slave manipulator/secondary platform instrument in the work site. The slave control signals may be produced by adding or multiplying a transform to the master signals, so that they can be implemented appropriately on the secondary platform instrument.

Embodiments of the present disclosure may facilitate control of secondary platform arms/instruments that have or are likely to have an orientation will difference such that direct implementation of received commands from an operator are likely to result in movements the opposite of those desired by the operator. Embodiments of the present disclosure are applicable to systems having separate bases, systems having different platforms but a common base, and to systems having instruments approaching work site from substantially opposite sides of the plane.

Embodiments of the present disclosure may be modified and such modifications are within the scope of the present disclosure. For example, some operational steps like operation 1702 and 1704 are depicted in a particular sequence, but may be performed in another sequence, such as performing operation 1704 before performing operation 1702. Accordingly, such modifications are within the scope and spirit of the present disclosure.

What is claimed is:

1. A teleoperational system comprising:
    a first manipulator configured to support an instrument moveable within an instrument workspace, the instrument having an instrument frame of reference;
    an operator input device configured to receive movement commands from an operator; and
    a control system, wherein to implement the movement commands, the control system is configured to:
        receive, via the operator input device, a first movement command from the operator,
        compare an orientation of the instrument with an orientation of a field of view of an imaging system to produce an orientation difference, the imaging system being configured to capture images of the instrument workspace,
        when the orientation difference does not meet an orientation criterion set:
            convert, based on a first movement command mapping, the first movement command to a first instrument motion in a first direction relative to the instrument frame of reference, and
            cause the instrument to move according to the first instrument motion, and
        when the orientation difference comparison meets the orientation criterion set:
            convert, based on a second movement command mapping, the first movement command to a second instrument motion in a second direction relative to the instrument frame of reference, and cause the instrument to move according to the second instrument motion,
wherein the second movement command mapping differs from the first movement command mapping.

2. The teleoperational system of claim 1, wherein the orientation criterion set comprises the orientation difference exceeding an orientation difference threshold.

3. The teleoperational system of claim 2, wherein the orientation difference threshold is greater than or equal to 135° and less than or equal to 225° relative to a centerline of the field of view.

4. The teleoperational system of claim 1, wherein the orientation criterion set includes an indication, stored in memory, that the first manipulator is associated with a secondary platform.

5. The teleoperational system of claim 1 wherein the control system is further configured to:
  in response to the orientation difference not meeting the orientation criterion set:
    convert, based on a third movement command mapping, the first movement command to a third instrument motion in a third direction relative to the instrument frame of reference, and
    cause the instrument to move according to the third instrument motion, and
  in response to the orientation difference meeting the orientation criterion set:
    convert, based on a fourth movement command mapping, the first movement command to a fourth causing instrument motion in a fourth direction relative to the instrument frame of reference, and
    cause the instrument to move according to the fourth instrument motion
    wherein the fourth movement command mapping differs from the third movement command mapping.

6. The teleoperational system of claim 1, further comprising a second manipulator configured to support an imaging sensor configured to provide the field of view, wherein:
  the first manipulator is supported by a first base,
  the second manipulator is supported by a second base, and
  the first and second bases are physically separate and are moveable relative to each other.

7. The teleoperational system of claim 6, wherein the first base is configured for mounting to a medical table.

8. The teleoperational system of claim 1, wherein the control system is further configured to:
  detect that the first manipulator is a secondary platform manipulator.

9. The teleoperational system of any claim 1, wherein the control system is configured to convert the first movement command to the first instrument motion or the second instrument motion by altering one or more directional components of the first movement command.

10. The teleoperational system of claim 9, wherein altering the one or more of the directional components of the first movement command comprises inverting the one or more of the directional components of the first movement command.

11. The teleoperational system claim 1, wherein the operator input device is aligned with a distal end of the instrument in the instrument frame of reference by an ergonomic offset.

12. The teleoperational system of claim 1, wherein the instrument moveable within the instrument workspace is a medical instrument moveable within a surgical site.

13. The teleoperational system of claim 1, wherein the first direction is an inversion of the second direction.

14. The teleoperational system of claim 1, wherein the control system is configured to compare the orientation of the instrument with the orientation of the field of view of the imaging system by:
  using the orientation of the first manipulator as the orientation of the instrument; and
  comparing the orientation of the first manipulator with an orientation of another manipulator that supports the imaging system providing the field of view.

15. The teleoperational system of claim 1, wherein the control system is configured to compare the orientation of the instrument with the orientation of the field of view by:
  determining an angle between a first axis characterizing the orientation of the instrument and a second axis characterizing the orientation of the field of view.

* * * * *

UNITED STATES PATENT AND TRADEMARK OFFICE
CERTIFICATE OF CORRECTION

| | |
|---|---|
| PATENT NO. | : 11,672,616 B2 |
| APPLICATION NO. | : 16/316859 |
| DATED | : June 13, 2023 |
| INVENTOR(S) | : Nicola Diolaiti |

It is certified that error appears in the above-identified patent and that said Letters Patent is hereby corrected as shown below:

In the Claims

Column 30, Claim 1, Line 62, please delete "comparison" after difference.

Signed and Sealed this
Eleventh Day of July, 2023

Katherine Kelly Vidal
*Director of the United States Patent and Trademark Office*